(12) United States Patent
Burman et al.

(10) Patent No.: US 12,733,843 B2
(45) Date of Patent: Sep. 15, 2026

(54) PERSONALIZED ASSISTANCE SYSTEM AND METHOD FOR INFRAMARKER-BASED MONITORING AND CONTROLLED RESPONSE

(71) Applicant: RCE Technologies, Inc., Carlsbad, CA (US)

(72) Inventors: Atandra Burman, Bermuda Dunes, CA (US); Jitto Titus, Acworth, GA (US); T David Gbadebo, Stone Mountain, GA (US)

(73) Assignee: RCE Technologies, Inc., Carlsbad, CA (US)

( * ) Notice: Subject to any disclaimer, the term of this patent is extended or adjusted under 35 U.S.C. 154(b) by 118 days.

(21) Appl. No.: 18/596,210

(22) Filed: Mar. 5, 2024

(65) Prior Publication Data

US 2024/0206776 A1 Jun. 27, 2024

Related U.S. Application Data

(63) Continuation-in-part of application No. PCT/US2022/049103, filed on Nov. 7, 2022, which is a continuation of application No. 17/537,932, filed on Nov. 30, 2021, now Pat. No. 12,201,419.

(Continued)

(51) Int. Cl.
*G16H 50/70* (2018.01)
*A61B 5/00* (2006.01)

(Continued)

(52) U.S. Cl.
CPC ........ *A61B 5/1455* (2013.01); *A61B 5/14546* (2013.01); *A61B 5/7264* (2013.01);

(Continued)

(58) Field of Classification Search
CPC . A61B 5/1455; A61B 5/14546; A61B 5/7264; A61B 5/318; G16H 40/60; G16H 50/20; G16H 50/70; A61K 45/00
See application file for complete search history.

(56) References Cited

U.S. PATENT DOCUMENTS 11,257,591 B2 2/2022 Burman et al.
11,969,577 B1 * 4/2024 Sahani .................. G16H 20/17

(Continued)

FOREIGN PATENT DOCUMENTS

WO 2025096995 A1 5/2025

*Primary Examiner* — Rachelle L Reichert
*Assistant Examiner* — Dawn Trinah Haynes
(74) *Attorney, Agent, or Firm* — Nayyer Siddiqi; Quinn IP Law

(57) ABSTRACT

A personalized assistance system includes an infrasensor device adapted to collect input data from a subject. A controller is configured to receive the input data from the infrasensor device. The controller has a processor and tangible, non-transitory memory on which instructions are recorded and is adapted to selectively execute one or more machine learning modules. Execution of the instructions by the processor causes the controller to extract one or more inframarkers from the input data. The controller is configured to determine respective changes in the inframarkers in real-time, including deviations from a respective baseline measurement customized for the subject. The controller is configured to determine at least one recommendation based in part on the inframarkers and the respective changes, via the one or more machine learning modules. The recommendation is executed when a predefined threshold is met.

20 Claims, 9 Drawing Sheets

Related U.S. Application Data

(60) Provisional application No. 63/488,750, filed on Mar. 6, 2023, provisional application No. 63/346,552, filed on May 27, 2022, provisional application No. 63/276,594, filed on Nov. 7, 2021.

(51) Int. Cl.

| | |
|---|---|
| ***A61B 5/145*** | (2006.01) |
| ***A61B 5/1455*** | (2006.01) |
| ***G16H 40/60*** | (2018.01) |
| ***G16H 50/20*** | (2018.01) |

(52) U.S. Cl.

CPC ............ *G16H 40/60* (2018.01); *G16H 50/20* (2018.01); *G16H 50/70* (2018.01)

(56) References Cited

U.S. PATENT DOCUMENTS

| | | | | |
|---|---|---|---|---|
| 12,138,051 | B2 | 11/2024 | Burman et al. | |
| 2015/0112168 | A1 | 4/2015 | Conrad et al. | |
| 2015/0268251 | A1* | 9/2015 | Zaugg | A61P 9/04 |
| 2017/0112991 | A1* | 4/2017 | Pudil | A61M 1/14 |
| 2017/0173262 | A1* | 6/2017 | Veltz | G16H 20/17 |
| 2018/0364163 | A1 | 12/2018 | Titus et al. | |
| 2019/0226912 | A1* | 7/2019 | Smith | G01J 3/0264 |
| 2020/0069860 | A1* | 3/2020 | Rammo | A61M 1/34 |
| 2020/0118679 | A1 | 4/2020 | Burman et al. | |
| 2020/0206422 | A1* | 7/2020 | Cassim | G16H 50/20 |
| 2020/0237305 | A1 | 7/2020 | Burman et al. | |
| 2020/0241019 | A1* | 7/2020 | Kim | G01N 33/92 |
| 2021/0059574 | A1* | 3/2021 | Shinohara | G01N 21/41 |
| 2021/0195891 | A1* | 7/2021 | Uygun | A01N 1/125 |
| 2021/0353203 | A1 | 11/2021 | Burman et al. | |
| 2021/0369148 | A1 | 12/2021 | Titus et al. | |
| 2021/0391081 | A1* | 12/2021 | Goldner | G16H 10/60 |
| 2022/0136956 | A1* | 5/2022 | Roberts | G01J 1/08 |
| 2023/0272056 | A1* | 8/2023 | Hsieh | C07K 16/22 |
| 2023/0386656 | A1* | 11/2023 | Huneker | G16H 50/20 |
| 2024/0293027 | A1 | 9/2024 | Burman et al. | |
| 2024/0298631 | A1 | 9/2024 | Burman et al. | |

* cited by examiner

PERSONALIZED ASSISTANCE SYSTEM AND METHOD FOR INFRAMARKER-BASED MONITORING AND CONTROLLED RESPONSE

CROSS REFERENCE TO RELATED APPLICATIONS

This application claims priority to and benefit of U.S. Provisional Application No. 63/488,750 filed Mar. 6, 2023. This application claims priority to and benefit of International Application No. PCT/US2022/049103 filed Nov. 7, 2022, which claims priority to U.S. Provisional Application No. 63/346,552 filed May 27, 2022, U.S. Non-Provisional application Ser. No. 17/537,932 filed Nov. 30, 2021, and U.S. Provisional Application No. 63/276,594 filed Nov. 7, 2021. The contents of each of the above-listed references is hereby incorporated by reference in their entireties.

TECHNICAL FIELD

The present disclosure generally relates to a personalized assistance system having inframarker-based monitoring, analysis, and controlled response, and method regarding the same.

BACKGROUND

The development of methods for evaluating complex medical situations while reducing the burden on health care facilities is a challenging matter. For example, assessing whether someone is having a heart attack may include taking blood samples which are sent to a laboratory for analysis. Delaying treatment while waiting for test results may worsen health outcomes. Therefore, it is desirable to provide a personalized non-invasive monitoring system that can streamline workflows, preferably with a rapid testing mechanism for timely analysis of different types of ailments, and a comprehensive system for responding to the results.

SUMMARY

Disclosed herein is a personalized assistance system having an infrasensor device adapted to collect input data from a subject. A controller is configured to receive the input data from the infrasensor device. The controller has a processor and tangible, non-transitory memory on which instructions are recorded and is adapted to selectively execute one or more machine learning modules. Execution of the instructions by the processor causes the controller to extract one or more inframarkers ("one or more" omitted henceforth) from the input data, via the one or more machine learning modules. The controller is configured to determine respective changes in the inframarkers in real-time, including deviations from a respective baseline measurement customized for the subject. The controller is configured to determine at least one recommendation based in part on the inframarkers and the respective changes, via the one or more machine learning modules. The recommendation is executed when a predefined threshold is met.

In some embodiments, the infrasensor device includes an optical sensor configured to provide an optical fingerprint of a biomarker, the optical sensor being adapted to be in transdermal contact with the subject. The infrasensor device may include an infrared source configured to generate light at a predetermined pulse rate and a photodetector configured to detect the light at a predetermined polling rate.

In some embodiments, a dialysis apparatus is selectively connected to the subject, the infrasensor device being positioned concurrently with dialysis. Here, the infrasensor device is positioned transdermally or integrated upstream or downstream of the dialysis apparatus or within respective components of the dialysis apparatus. The controller may be employed in post-dialysis drug re-equilibration, including monitoring changes in drug concentration in the subject post-dialysis.

In some embodiments, an extracorporeal membrane oxygenation (ECMO) apparatus is selectively connected to the subject. The ECMO apparatus includes a pump and an oxygenator. The infrasensor device is positioned concurrently with dialysis. The infrasensor device is positioned transdermally or integrated upstream or downstream of the ECMO apparatus or within respective components of the ECMO apparatus. The controller is adapted to generate automatic threshold-based trigger notifications to the ECMO apparatus for optimal drug dosing for the subject based in part on the respective changes in the one or more inframarkers.

The system may include a patient activator in communication with the controller, the patient activator including a display and/or audio output for communication with the subject. Executing the recommendation includes providing messages and/or alerts to the subject, including dosage modulation instructions, via the patient activator. The system may include an injection device in communication with the controller and adapted to deliver a therapeutic medication to the subject. executing the recommendation includes automatic adjustment of the therapeutic medication to the subject, via the injection device. The injection device may be an analgesia pump for pain management.

In some embodiments, the controller is adapted to calculate a therapeutic dosage appropriate to a detected acuity level of the inframarkers. The therapeutic medication includes at least one of thrombolytics, anticoagulants, antiplatelets, thrombolytics coupled with antiplatelets, the therapeutic medication being automatically administered when the detected acuity level exceeds a threshold. In some embodiments, the inframarkers include troponin, and the therapeutic medication includes at least one of beta blockers, calcium channel blockers, loop diuretics, and spironolactones.

In some embodiments, the inframarkers include myocardial injury inframarkers where the subject is receiving immune checkpoint inhibitor therapy. Here executing the recommendation includes automatic down-titration of the immune checkpoint inhibitor therapy and initiating a modulated steroid therapy, when the inframarkers exceed a predefined ceiling.

The controller may be adapted to monitor cancer progression and/or therapy resistance for the subject based in part on the inframarkers. Here, the inframarkers include at least one of extracellular vesicles, co-receptors for growth factors, cell surface receptor adaptor proteins, transcription factors, and scaffolding proteins. The controller may be adapted to assess cardiotoxicity in the subject based in part on the inframarkers, including troponin.

In some embodiments, the subject is an organ selected for transplantation, with the inframarkers including myocardial injury biomarkers during transport and storage of the organ. The organ is preserved with at least one cyroprotective agent. Here, executing the recommendation includes modulating a level of the cryoprotective agent based on the inframarkers. A GPS receiver may be adapted to detect location of the infrasensor device. Executing the recommendation may include automatic notification of a remote assistance service provider.

Disclosed herein is a method for operating a personalized assistance system having a controller with a processor and tangible, non-transitory memory on which instructions are recorded. The method includes collecting input data from a subject via an infrasensor device electronically coupled with the controller. The input data is transmitted to the controller. The method includes extracting one or more inframarkers from the input data, via execution of a software application by the controller. The method includes determining respective changes in the inframarkers in real-time, via the controller, including deviations from a respective baseline measurement customized for the subject. The method includes determining at least one recommendation based in part on the one or more inframarkers and the respective changes, via execution of one or more machine learning modules by the controller. The method includes executing the recommendation when a predefined threshold is met.

The above features and advantages and other features and advantages of the present disclosure are readily apparent from the following detailed description of the best modes for carrying out the disclosure when taken in connection with the accompanying drawings.

Figure 1:
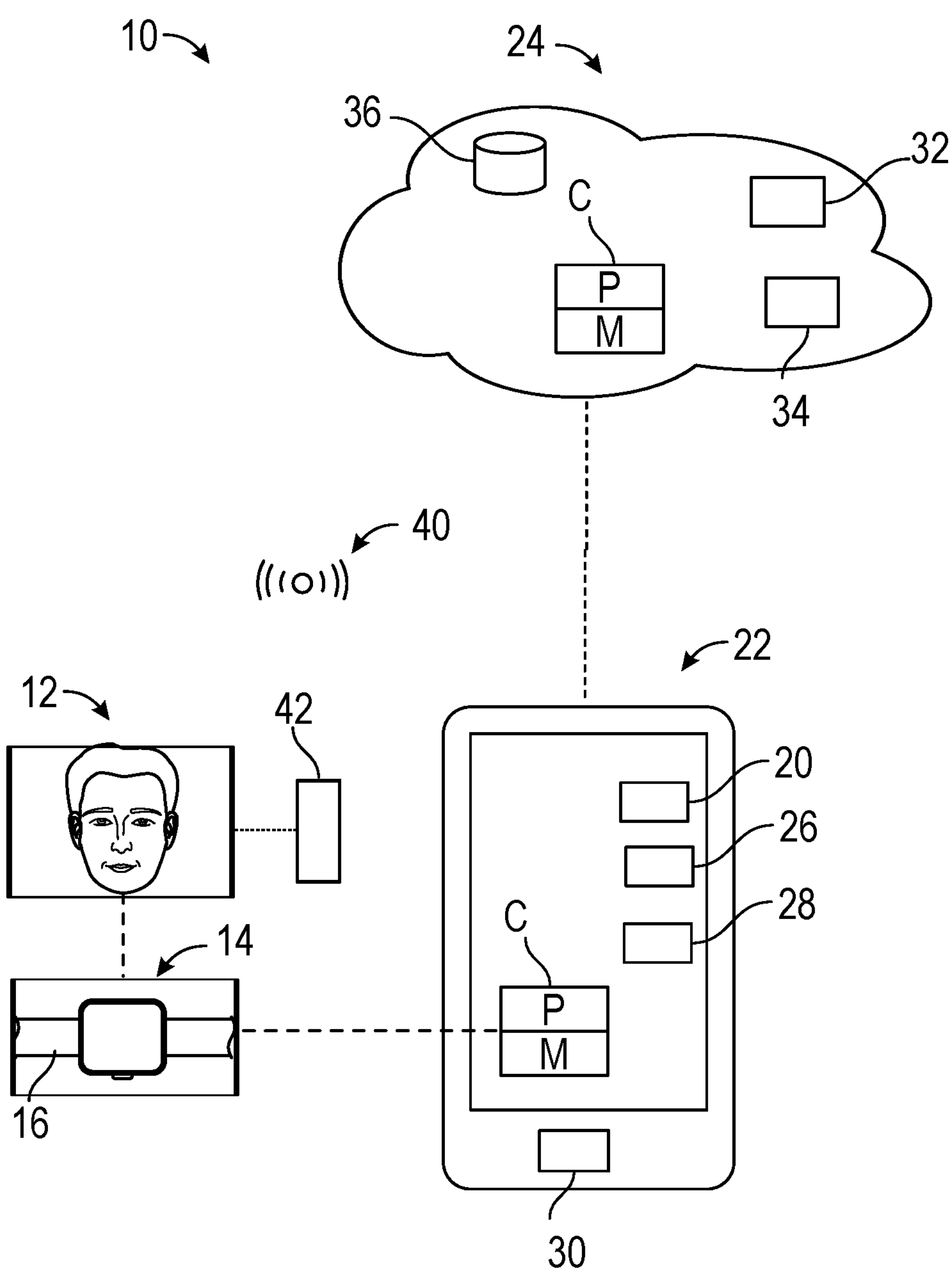
FIG. 1 is a schematic diagram of a personalized assistance system with inframarker-based monitoring using an infrasensor device, the system having a controller.

Representative embodiments of this disclosure are shown by way of non-limiting example in the drawings and are described in additional detail below. It should be understood, however, that the novel embodiments of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

In the following description, numerous details of the embodiments of the present disclosure, which should be deemed merely as exemplary, are set forth with reference to accompanying drawings to provide thorough understanding of the embodiments of the present disclosure. Therefore, those skilled in the art will appreciate that various modifications and replacements may be made in the described embodiments without departing from the protection scope and the spirit of the present disclosure. Further, for clarity and conciseness, descriptions of known functions and structures are omitted hereinafter.

Referring to the drawings, wherein like reference numbers refer to like components, FIG. 1 is a schematic diagram illustrating a personalized assistance system 10 (henceforth "system") for monitoring a subject 12. The system 10 includes an infrasensor device 14 adapted to collect input data from the subject 12. In some embodiments, the infrasensor device 14 may be embedded in a wearable device 16 providing transdermal, non-percutaneous contact between the subject 12 and the infrasensor device 14. An example infrasensor device 14 is shown in and described below with respect to FIG. 2. Additionally, the infrasensor device 14 can analyze the subject 12 by analyzing body fluids of the subject 12 in a transdermal manner. Bodily fluids of the subject 12 may include blood, intestinal fluid, etc.

Figure 3:
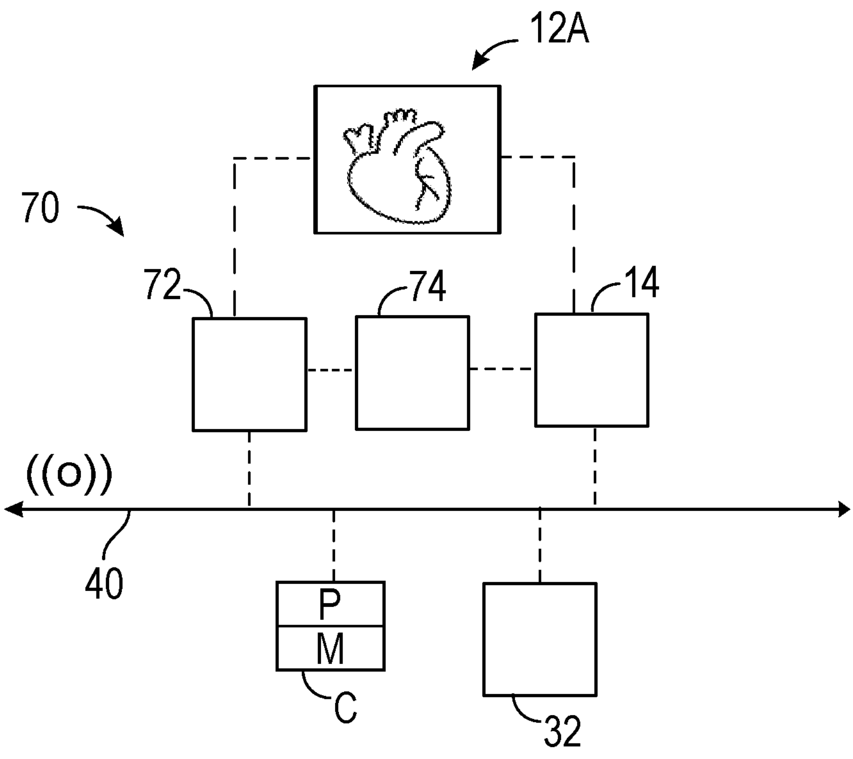
FIG. 3 is a schematic diagram of an example configuration for the system of FIG. 1, with an in-line infrasensor device.

The subject 12 can be a human subject who is being analyzed to predict if the subject 12 has a particular physiological condition, or at least an infraspectral marker. As described below, the subject 12 may be an organ 12A as shown in FIG. 3, such as a heart donated for transplantation. Example configurations for the system 10, with an in-line infrasensor device are shown in and described below with respect to FIGS. 3-4.

The system 10 is adapted to employ infrared optics to discover infraspectral markers, which may be associated with one or more diseases. An infraspectral marker can also be referred to herein as an inframarker. For example, the presence of one or more infraspectral markers in a transdermal scan of a subject 12, performed according to one or more embodiments described herein, can be mapped to a disease or physiological state of the subject, such as, cancer, diabetes, a chronic condition, a comorbidity, a rare disease, or any other condition. An "inframarker" as used herein is an optical infrared signature representative of a biomarker e.g., troponin-I. An inframarker can be any form of infrared signature such as an absorption, a transmission, a reflection, or a combination thereof. For example, a unique combination of absorption peaks from an infraspectral scan can be inframarkers for biomarkers such as, h-FABP (fatty acid binding protein) or CEA (carcinoembryonic antigen). It is understood that other types of inframarkers and biomarkers can be used in other embodiments of the technical solutions described herein. Further, "an infraprofile" refers to an optical infrared signature representative of a physiological condition e.g., myocardial infarction. An infraprofile can include one or more inframarkers. For example, a physiological condition can be represented by one or more biomarkers, and accordingly, the infraprofile for that physiological condition includes the corresponding one or more inframarkers. It will be appreciated that an inframarker may not necessarily have to represent a known biomarker. Some embodiments of the technical solutions described herein can identify a unique inframarker profile that represents a physiological state of the subject 12 without corresponding to any known biomarker. In other words, the infraprofile facilitates identifying a physiological state of the subject 12 directly (without having to determine a corresponding biomarker).

Referring to FIG. 1, the personalized assistance system 10 includes a controller C having at least one processor P and at least one memory M (or non-transitory, tangible computer readable storage medium) on which are recorded instructions for executing a method 100, which is shown and described below with reference to FIG. 5.

As will be described below, a controller C is configured to receive the input data from the infrasensor device 14. The controller C is adapted to extract one or more inframarkers from the input data. The controller C has access to and is specifically programmed to selectively execute one or more machine learning models 20, described in detail below. The machine learning models 20 may be configured to find parameters, weights or a structure that minimizes a respective cost function. In some embodiments, the inframarkers can be analyzed using the machine learning models 20.

The controller C is configured to determine respective changes in the inframarkers in real-time, including deviations from a respective baseline measurement customized for the subject 12. The controller C is configured to determine at least one recommendation based in part on the inframarkers and the respective changes, via the machine learning modules 20. The recommendation is executed when a predefined threshold is met.

Referring to FIG. 1, the controller C may be in communication with a cloud unit 24. Alternatively, the controller C and/or the machine learning models 20 may be embedded in a cloud unit 24. The cloud unit 24 may include one or more servers hosted on the Internet to store, manage, and process data. may be embedded in a cloud unit 24. It should be noted that although the controller C is shown separate from the infrasensor device 14, in one or more examples, the controller C can be part of the infrasensor device 14 itself (or vice versa). In the cases where the controller C is separate from the infrasensor device 14, the controller C can be embedded within a connected or smart device 22.

Referring to FIG. 1, the smart device 22 may be a smartphone, laptop, tablet, desktop or other electronic device. The smart device 22 may include a respective processor and a respective memory and may run one or more applications, which may be mobile applications or "apps." In some embodiments, the smart device 22 may include a patient notification app 26 having a visual display and/or audio output for communicating with the subject 12. Executing the recommendations may include providing messages and/or alerts to the subject 12, including dosage modulation instructions, via the patient notification app 26.

Referring to FIG. 1, the smart device 22 may include a GPS receiver 28 adapted to detect location of the infrasensor device 14. Executing the recommendation can include automatic notification of the location of the subject 12 to a remote assistance service provider. Alternatively, the GPS receiver 28 may be embedded within the infrasensor device 14. Referring to FIG. 1, the smart device 22 may be operated by the subject 12 via a user interface 30, which may be a touch screen interface or I/O device such as a keyboard or mouse. As described below, the cloud unit 24 may include various software applications 32 and/or artificial intelligence models 34. The cloud unit 24 can further include a database 36 for storing respective information pertaining to a group of subjects.

The appropriate response (e.g., treatment with medication) is applied to the subject 12 based on the detection of one or more infraspectral markers ("inframarkers"). The controller C (via execution of the various software programs and machine learning modules 20) may function as a transdermal biomarker detection platform that uses one or more infraspectral markers, an inframarker profile that is based on the infraspectral markers, and an inframarker configuration for the infrasensor device 14. An inframarker profile can also be referred to herein as an infraprofile. The inframarker configuration for the infrasensor device 14 can be configured or set in various ways. In an illustrative example, the inframarker configuration can be a representation of a disease journey (series of disease phenotypes).

Figure 2:
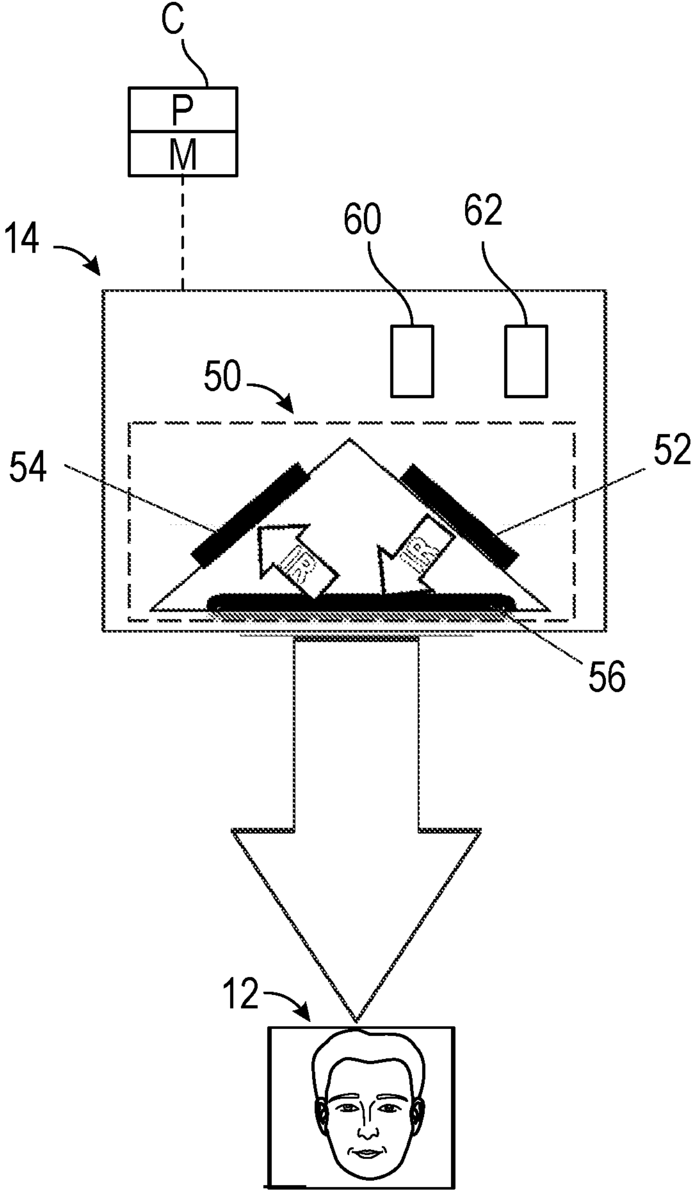
FIG. 2 is a schematic diagram of an example infrasensor device employable in the system of FIG. 1.

Referring now to FIG. 2, a schematic diagram of an example infrasensor device 14 is shown. The infrasensor device 14 is configured to be in transdermal contact with the subject 12. The infrasensor device 14 has an optical sensor 50 that employs spectroscopy in the near, mid, and far-infrared range, microwave range, visible region, or other such range of the electromagnetic spectrum. The range can be varied based on the biomarker (i.e., protein or chemical) being predicted.

The optical sensor 50 is adapted to employ infrared (IR) spectroscopy to provide an optical fingerprint of a biomarker when scanned in the 2000 to 800 cm-1 (5 μm to 12.5 μm) range. This detection can be used to identify, differentiate and quantify the amount of the biomarkers (for example, troponin I, FABP3, etc.) in whole blood. An inframarker is a fingerprint for a biomarker and can be a unique combination of absorbance peaks within a spectral range in which the concentration of the biomarker in a biofluid can be detected using the optical sensor 50. Absorbance peaks are monitored based on amplitude of the reflected light that is absorbed by a photodetector in the optical sensor 50 in one or more examples.

In the example shown, the optical sensor 50 includes an infrared source 52, a photodetector 54, and an internal reflection element 56. The infrared source 52 can include lasers, light emitting diodes (LEDs), radiative light sources, or other such sources of light configured to generate light at a predetermined pulse rate. The infrared source 52 may transmit infrared light of a particular wavelength based on a voltage that is applied to the infrared source 52 and controlled by a processing unit 62. The processing unit 62 applies a particular voltage depending on the biomarker that is being detected by the processing unit 62. The infrasensor device 14 includes a processing unit 62, a memory 60, and can include other components such as connectors, communication devices, and the like, which are not shown. The processing unit 62 can include one or more microprocessors that can execute computer executable instructions. The memory 60 is a volatile and/or non-volatile memory device that can store the computer executable instructions in addition to data items such as media, text, databases, data structures, files, and other electronic data that facilitates the operation of the infrasensor device 14.

Referring to FIG. 2, the photodetector 54 is paired with the infrared source 52 and can include quantum wells, quantum dots, bolometers, and the like. In one or more examples, the photodetector 54 generates a voltage or an electric current as an output signal, which is proportional to an amount of light incident on the photodetector 54, after some of the light is absorbed by the subject 12. The photodetector 54 may be configured to detect the incident light at a predetermined polling rate.

The photodetector 54 is adapted to provide absorption measurements of the infrared light from the body fluid(s) of the subject 12. For detecting particular biomarkers one or more absorbance peaks may be identified at predetermined wavelengths of the infrared light. For example, two absorbance wavelength ranges, 5.5 to 6.6 μm and 8.3 to 11.8 μm are sensitive and specific to FABP3 in whole blood. Further, three absorbance wavelength ranges for troponin in whole blood are 5.5 μm to 7.8 μm, 8.8 μm to 10.3 μm, and 10.5 to 12 μm. The infrared source 52 uses such predetermined wavelengths to facilitate detection of the corresponding biomarkers. It is understood that the above-described values are examples and that in one or more examples, different and/or additional wavelengths and/or ranges can be used.

In the example shown in FIG. 2, the optical sensor 50 includes an internal reflection element 56 (henceforth "IRE") that is made of particular material(s) to facilitate the optical sensor 50 to detect the biomarker(s). For example, the IRE 56 can be made of low-density polyethylene, diamond, ZnSe, Ge, Si etc. The IRE 56 is formed such that the infrared light from the infrared source 52 is incident at an angle equal to or lesser than the critical angle associated with the IRE material to allow total internal reflection of the infrared light. The critical angle is dependent on the material of the IRE 56. Further, the refractive indices of the IRE 56 and of the sample being analyzed, coupled with the wavelength of infrared light dictate the penetration depth of the infrared light into the tissue, blood (or any other body fluid) of the subject 12. As described below, the controller C is adapted to determine whether a biomarker is present in the subject 12 based on the absorption measurement. The controller C may stratify the subject 12 based on the absorption measurement. It is understood that other optical components and filters such as notch filters (selective wavelength) and polarizers may be employed by the optical sensor 50 to improve the selectivity and sensitivity of the optical sensor 50 when detecting the biomarker.

In some embodiments, the optical sensor 50 scans the body fluid of the subject 12 in a transdermal manner. The infrasensor device 14 is in contact with the subject 12, for example, in contact with the skin of the subject 12, to facilitate the scanning by the sensor 50. The infrasensor device 14, using the optical sensor 50 transdermally detects one or more characteristics, such as proteins or other types of chemicals in the human body, for example, in the blood flow and interstitial fluids. The optical sensor 50 of the infrasensor device 14 is not limited to an optical scanner and may include ECG sensors, haptic sensors, audio sensors, biosensors, and other types of sensors.

FIG. 3 is a schematic diagram of an example configuration for the system 10, with an in-line infrasensor device. In this embodiment, an extracorporeal membrane oxygenation (henceforth "ECMO") apparatus 70 selectively connected to a subject or organ 12A (heart in this example). The ECMO apparatus 70 includes a pump 72 and an oxygenator 74, for pumping and oxygenating the blood of the outside the body, allowing the heart and lungs to rest. Here the infrasensor device 14 may be positioned inline upstream or downstream of the ECMO apparatus 70 or within the components of the ECMO apparatus 70.

The infrasensor device 14 may be concurrently (with respect to the time of dialysis) positioned transdermally, or integrated upstream or downstream of the dialysis apparatus. "Concurrently" refers to the time of placement of the infrasensor device 14 with respect to the time of dialysis. During dialysis, the infrasensor device 14 can collect information transdermally on the body of the subject, or it could also be used by integrating the device into the blood-transporting channels of the dialysis equipment either before or after it enters the dialysis equipment. Infrared transdermal interrogation is defined here as a medical and health monitoring technique that uses infrared technology to assess various body-related parameters without penetrating the skin or requiring blood samples.

The controller C can be adapted to monitor for infection, myocardial damage, and/or myocardial burden/ischemia. The controller C can be adapted to generate automatic threshold-based trigger notifications to the ECMO apparatus 70 based in part on the respective changes in the inframarkers, such as troponin. Infrasensor monitoring can generate automatic threshold based trigger notifications in analyzing effectiveness of therapy, and modulating pharmacokinetics and pharmacodynamics of analgesics and sedatives such as propofol, digoxin, midazolam, or opioids. Higher doses of sedatives and analgesics can then be administered to obtain an appropriate sedation and comfort of the patient. Hence, protocols of management of pain, sedation, and other medications can be reassessed for ECMO patients.

Referring to FIG. 3, in another embodiment, the subject may be an organ 12A selected for transplantation. Transporting tissues and organs from the site of donation to the patient in need, while maintaining viability, is a limiting factor in transplantation medicine. Cyroprotective agents are instrumental in hypothermic preservation. Paradoxically, preserving the health of organs during transport and organ storage can be compromised by cyroprotective agent toxicity. Inframarker tracking of myocardial injury biomarkers during transport and heart bank storage, can feed into computational models that inform the optimal method of hypothermic machine perfusion with multiple steps of loading/unloading cyroprotective agents in order to reduce the toxicity and osmotic damage to organs other than heart (such as lung, kidney, liver etc.) In other words, the inframarkers here include myocardial injury biomarkers during transport and storage of the organ, the organ being preserved with cyroprotective agents. Executing the recommendation can include modulating levels of the cyroprotective agents based on the inframarkers.

Figure 4:
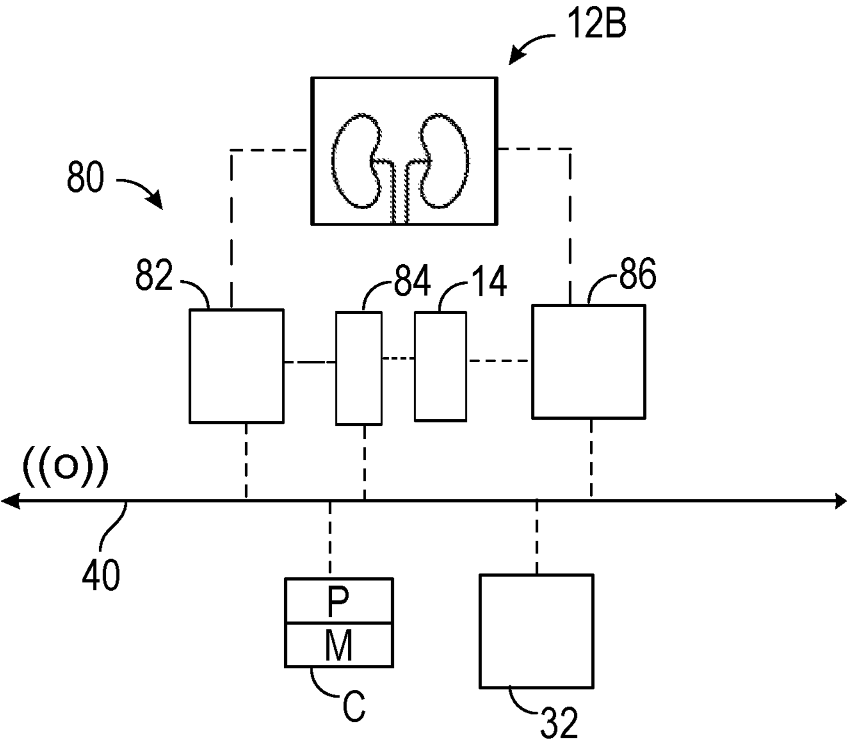
FIG. 4 is a schematic diagram of another example configuration for the system of FIG. 1, with an in-line infrasensor device.

FIG. 4 is a schematic diagram of another configuration for the system 10, with an in-line infrasensor device. In this embodiment, a dialysis apparatus 80 is selectively connected to a patient 12B. The system 10 may be employed in post-dialysis drug re-equilibration in hemodialysis patients in a dialysis clinic or peritoneal dialysis patients at home. This can be achieved by monitoring changes in drug concentration produced by dialysis. The dialysis apparatus 80 includes a pressure monitor/pump 82 that keeps the blow flow at a suitable rate. Blood from the patient 12B enters a dialyzer 84, where it is filtered. A dialysate solution is entered into the dialyzer 84 to draw the waste out of the blood. The used dialysate solution is pumped out of the machine and discarded.

The infrasensor device 14 may be positioned inline upstream or downstream of the dialysis apparatus or within the components of the dialysis apparatus 80. The infrasensor device 14 can be positioned within a catheter 86 connected to the patient 12B, such that it is in contact with the blood. The infrasensor device 14 can be positioned in a dialysis solution bag used to drain the dialysate after dialysis. Levels in circulation via transdermal monitoring can be recalibrated and titrated back based upon the real-time levels cleared through the dialysis bags via transmembrane monitoring. The controller C can be employed in post-dialysis drug re-equilibration, including monitoring changes in drug concentration in the subject 12 post-dialysis. The subject 12 may be, for example, hemodialysis patients in a dialysis clinic or peritoneal dialysis patients at home.

The embodiments described herein enable remote patient monitoring. For example, the infrasensor device 14 can be used by the subject 12 when s/he is away from a medical institution (e.g., hospital, research institute, etc.). The measurements from the infrasensor device 14 can be transmitted to the controller C, which may or may not be remote from the infrasensor device 14, via the network 40. The infraprofile that is generated may be transmitted to a medical personnel, who may be remote from the subject (and hence, infrasensor device 14) and suggest the further course of action for the subject 12. Also, the controller C may analyze the measurements and apply and/or cause further treatment to be applied.

Referring to FIG. 1, in some embodiments, the system 10 includes an injection device 42 adapted to deliver a therapeutic dose to the subject. Executing recommendation includes automatic adjustment of the therapeutic dose to the subject, via the injection device 42. The therapeutic dose can include at least one of thrombolytics, anticoagulants, antiplatelets thrombolytics coupled with antiplatelets, the therapeutic medication being automatically administered when the detected acuity level exceeds a threshold.

In some embodiments, the system 10 can perform automodulation of beta blockers, calcium channel blockers, loop diuretics, spironolactones etc based upon transdermally monitored inframarker levels for cardiac proteins such as troponin and electrolyte anomalies. This may be useful, for example, in cases with Left Ventricular Assist Devices (LVAD), where levels of atrial natriuretic peptide (ANP) and brain natriuretic peptide (BNP) are naturally reduced from the ventricles, and hence the natural kidney regulation in the subject 12 is compromised.

The recommended therapeutic agents could be self-administered by patients or integrated as an automated injection device 42. An example could be automated administration of a thrombolytic during a silent heart attack in a high-risk coronary artery disease patient in the middle of the night or early hours of the morning when cortisol levels could trigger a cascade of atherosclerotic events.

For a subject 12 who is transitioning from chronic stable ischemic heart disease to acute coronary syndrome, the levels of thrombolytics or anticoagulants or antiplatelets may be modulated by the system 10 until clinical attention in geographically feasible locations is available. Similarly, thrombolytics coupled with antiplatelets and/or anticoagulants dosage could be recommended for remote applications until in-person clinical care can be administered. Additionally, the controller C may automatically inform a remote emergency service provider if the controller C determines that the detected inframarkers presents a potential danger to the subject, and if and when a therapeutic dosage was modulated. As noted above, the system 10 can include a GPS receiver 28 that detects the location of the infrasensor device 14, which is transmitted to the remote emergency service activating time-sensitive acute cardiac care workflows.

In some embodiments, the injection device 42 is an analgesia pump for pain management. The controller C can be adapted to calculate a therapeutic dosage appropriate to a detected acuity level of the one or more inframarkers. Additionally, the system 10 can be adapted for real-time monitoring of electrolyte imbalances and inotropes, and modulating kidney diuretics and cardiac drugs to manage blood pressure (e.g., antiarrhythmic agents based upon potassium thresholds).

In some embodiments, the controller C can be adapted to assess cardiotoxicity in the subject 12 based in part on the inframarkers. Here the inframarkers include cardiac troponin, a specific protein that enters the bloodstream when the heart muscle becomes damaged, such as during a heart attack. The therapeutic medication can include beta blockers, calcium channel blockers, loop diuretics, and spironolactones.

Transdermally derived inframarkers can further advance precision medicine with monitoring for cancer metastasis. In some embodiments where the subject 12 is undergoing cancer treatment, the controller C is adapted to monitor cancer progression and/or therapy resistance for the subject based in part on the inframarkers. Here inframarkers can include extracellular vesicles, co-receptors for growth factors, cell surface receptor adaptor proteins, transcription factors, and scaffolding proteins. Close tracking of baselines for specific cell signaling biomarkers such as proteins linked to epithelial-to-mesenchymal transition and the inframarkers mentioned above can inform proactive cancer therapeutics. Infrasensor enabled exosomal tracking of cell signaling markers to monitor cancer progression and therapy resistance can be used to enable modulating retrograde therapeutic dosage.

In some embodiments where the subject 12 receiving immune checkpoint inhibitor therapy, the controller C is adapted to detect myocardial injury inframarkers. When the inframarkers exceed a predefined ceiling, the controller C can be adapted to recommend automatic titration of the immune checkpoint inhibitor therapy and alongside titrated initiation of steroid therapy. Approximately 1% of cancer patients receiving immune checkpoint inhibitor therapy (hereinafter "ICI") therapy develop symptoms and are diagnosed for stage 3/4 myocarditis. When myocarditis is detected, these patients are paused on ICI therapy and started on modulated steroid therapy (modulated in the dosage, timing of starting and stopping the steroid) to contain their inflammation (myocarditis). The 6-9 weeks of steroid therapy may be complemented with weekly (blood-based) troponin measurements in the hospital, allowing cardio-oncologists to determine when to wean off the steroids and resume ICI therapy. This is a critical period when cancer patients are without ICI therapy, and in an immune-compromised state with steroid therapy.

Real-time inframarker monitoring can enable earlier detection of myocarditis (stage 1/2), and result in beneficial, potentially earlier modulation for ICI therapy. Modulating ICI therapy closely with myocardial injury inframarkers can posit early administration of therapeutic agents to manage and contain myocarditis before it becomes fulminant. This could improve adverse outcomes from cardiac causes. Additionally, monitoring for a return of biomarker levels to a non-acute baseline module therapy improves patient experience and an earlier return to ICI therapy, so as to facilitate better oncological management and outcomes in these patients.

Figure 5:
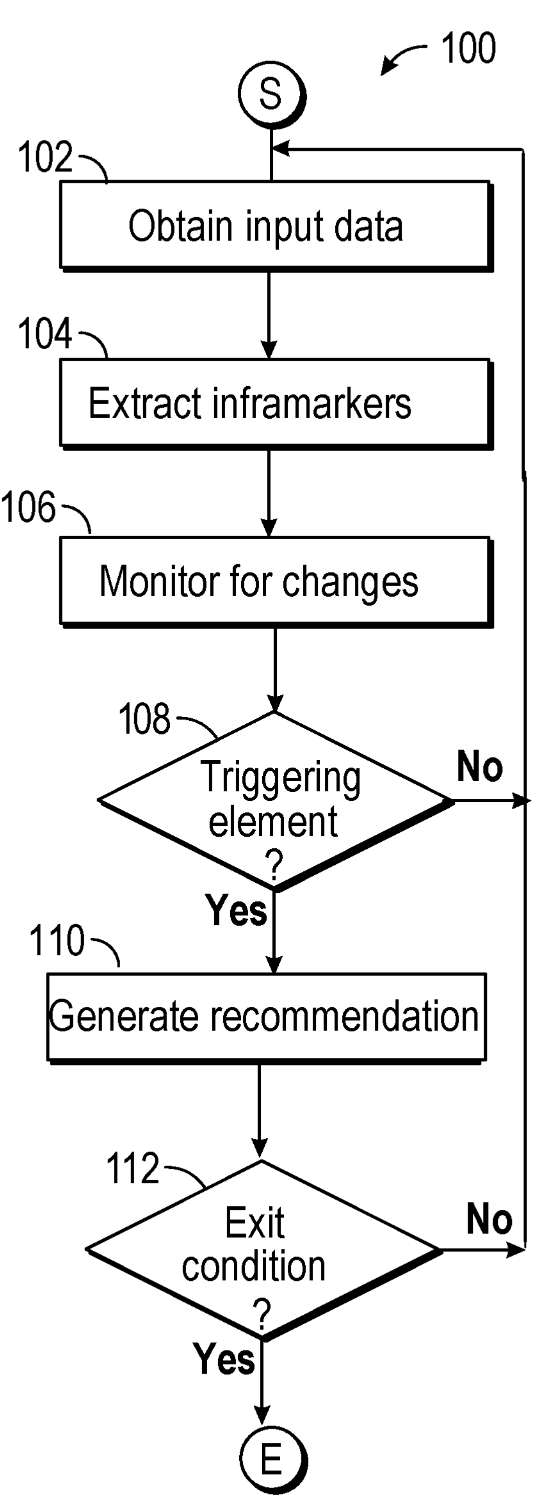
FIG. 5 is a schematic flow diagram of a method executable by the system of FIG. 1.

Referring now to FIG. 5, a flowchart of the method 100 stored on and executable by the controller C of FIG. 1 is shown. Method 100 may be embodied as computer-readable code or instructions stored on and partially executable by the controller C of FIG. 1. Method 100 need not be applied in the specific order recited herein. Furthermore, it is to be understood that some steps may be eliminated. The method 100 may be dynamically executed. As used herein, the terms 'dynamic' and 'dynamically' describe steps or processes that are executed in real-time and are characterized by monitoring or otherwise determining states of parameters and regularly or periodically updating the states of the parameters during execution of a routine or between iterations of execution of the routine.

Per block 102 of FIG. 2, the controller C is configured to obtain input data from the infrasensor device 14 via the network 40. Advancing to block 104 of FIG. 5, the method 100 includes performing feature extraction and analyzing for inframarkers on the input data. The controller C is configured to perform feature extraction by capturing (after scanning by the infrasensor device 14) the desired infraspectral markers that correlate to the inframarker configuration of interest. The infrasensor device 14 may be set for the inframarker configurations that scans the patients for the inframarkers associated with the cystic fibrosis disease profile, such as inframarker configurations A, B, C. The controller C can be configured to receive the inframarkers from the infrasensor device(s) 14 and determine inframarker profiles for each stage of the disease. The software application 32 may compare the received inframarker profiles of the patients in the cohorts to the known health conditions for the respective patients, in order to determine the effectiveness of respective drug A, drug B, and/or drug A and drug B. According to the response of the treatment, the controller C can determine which drugs and/or drug combination is beneficial for the treatment of each specific condition.

The controller C can be configured to receive the inframarkers from the infrasensor device 14 and determine inframarker profiles for each stage. The controller C may compare the received inframarker profile of the subject 12 to a previously known inframarker profile for the heart stored in one or more databases 36, in order to determine which patho-physiological phase the subject 12 is experiencing.

Proceeding to block 106 of FIG. 5, the controller C is adapted to analyze the data, including determining respective changes in the inframarkers in real-time, such as deviations from a respective baseline measurement customized for the subject 12. The controller C may provide feedback based on the respective changes to the subject 12 and/or health care providers.

Figure 6:
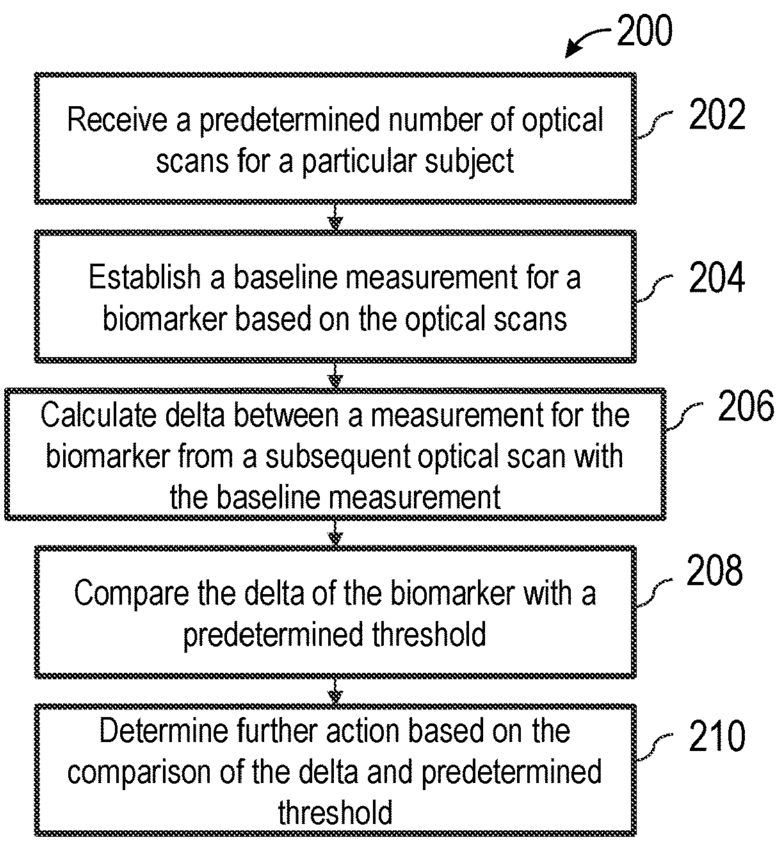
FIGS. 6-7 are schematic flow diagrams of analysis modules executable by the controller of FIG. 1.

Referring now to FIG. 6, a flowchart of an analysis module 200 for analyzing the input data (per block 104 of method 100) is shown. The analysis module 200 may be embodied as computer-readable code or instructions stored on and partially executable by the controller C of FIG. 1. The analysis module 200 includes, at block 202, receiving, by the controller C, data from at least a predetermined number of optical scans performed on a particular subject 12. The predetermined number can be 5, 10, 15, or any other number that the controller C can use to establish a personalized baseline measurement for the subject 12. The data from the optical scans, which can also be referred to herein as input data data, can be saved to the database 36, and as previously described, can be associated in the database 36 with subject-related information of the particular subject 12.

Proceeding to block 204, the controller C establishes the baseline measurement for at least one inframarker, i.e., biomarker (e.g., troponin I) using the optical scans, e.g., the input data data collected during optical scans of the subject 12 using the infrasensor device 14. The baseline measurement is established using a statistical technique such as calculating the mean, geometric mean, weighted mean, trendline computation, logistic regression, or any other linear or non-linear statistical computation. In some embodiments, the baseline is established using the machine learning modules 20, for example, using algorithms such as multi-parameter deep neural network described in detail below.

In some embodiments, when using machine learning to establish the baseline, the controller C automatically adjusts the infrasensor device 14. The configurability of the infrasensor device 14 can facilitate adjusting one or more settings such as delta value, wavelength of the light emitted and/or detected, intensity of light, electric voltage, electric current, pulse rate of the light emitter, pulse rate of the light receiver, etc. Here, the delta value is used to compare deviations of the measurements from the personalized baseline(s), and in response to the deviation being larger than the delta value, triggering one or more actions as described herein.

The controller C can conduct a predetermined number of optical scans of the subject 12 using a particular inframarker configuration, i.e., settings of the infrasensor device 14. The captured optical scans are analyzed to establish the baseline measurements. If a satisfactory baseline measurement (e.g., comparing with ground truth data) cannot be established for a physiological identifier of the subject 12 using the machine learning algorithm, the inframarker configuration of the infrasensor device 14 is adjusted by the controller C, and the baseline establishment is repeated using the machine learning. Such a process is repeated until a satisfactory baseline is established for a physiological marker of the subject 12. In some examples, a baseline measurement is established for multiple physiological markers for the subject in this manner.

Proceeding to block 206, data from subsequent optical scans by the infrasensor device 14 is compared by the controller C with the established baseline to calculate a difference between a measurement corresponding to the physiological identifier (e.g., biomarker) being observed with the baseline measurement. It should be noted that in some embodiments, the difference can be based on measurements of multiple parameters. For example, the physiological identifier can be based on measurements of two or more units of wavelengths. Accordingly, the delta can be based on (e.g., mean, sum, median, etc.) of the differences between measurements of the two or more parameters in a transdermal optical scan and corresponding baseline measurements.

Proceeding to block 208, the calculated difference is compared with a predetermined threshold, i.e., the delta value. If the difference exceeds the delta, a spike or a dip can be identified. In some embodiments, an absolute value (modulus) of the difference is used to compare with the delta.

Proceeding to block 210, a further action is determined based on the comparison of the difference and the delta. For example, if a spike/dip is not identified, i.e., the difference does not exceed the delta value, the continuous monitoring is continued. Alternatively, if a spike/dip is detected, additional tests may be performed on the subject 12. In yet other embodiments, in case of the spike/dip being detected, the configuration of the infrasensor device 14 is adjusted to perform additional optical scans on the subject 12. In some examples, if the difference exceeds the delta only by a minimal amount (e.g., a second predetermined value), the configuration of the infrasensor device 14 is adjusted automatically to detect fluctuations and/or variations from the baseline. In some embodiments, if the delta is exceeded, a notification to the medical personnel and/or to the subject 12 can be triggered. The notification can be transmitted, for example, via a display or interface accessible by the medical personnel and/or the subject 12, or via an alert output by the infrasensor device 14.

Advancing to block 108 of FIG. 5, the method 100 includes determining if a trigger element has been activated, e.g., if the difference exceeds the delta. If the trigger element has been activated (Block 108=YES), the method 100 proceeds to block 110 where the controller C is adapted to determine a recommendation or response. Recommendations can include treatment/medicine to be administered for the subject 12 (i.e., patient). The recommendation is executed when a predefined threshold is met. The predefined threshold may be varied based on the application at hand, e.g., according to the specific patho-physiological phase detected. If the trigger element has not been activated (Block 108=NO), the method 100 loops to block 102.

From block 110 of FIG. 5, the method 100 advances to block 112 to determine if a predefined exit condition is satisfied. The exit condition can include a decision to end monitoring of the subject 12 by a health care provider. Where the subject 12 is a donated organ, the exit condition includes the transplantation of the donated organ. If the exit condition is satisfied (Block 112=YES), the method 100 ends. If not (Block 112=NO), the method 100 loops to block 102.

Figure 7:
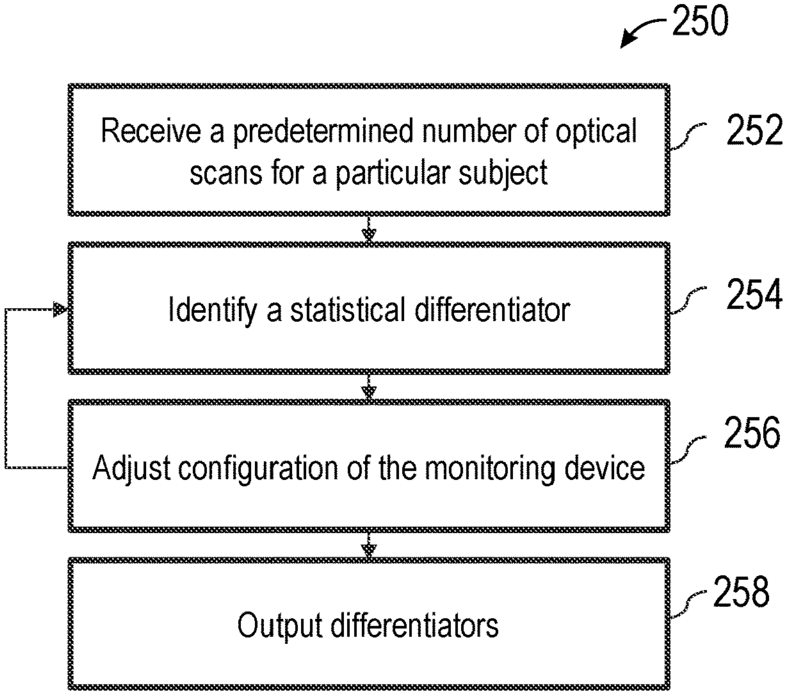

Referring now to FIG. 7, a flowchart of another example analysis module 250 for analyzing the input data (per block 104 of method 100) is shown. Analysis module 250 may be embodied as computer-readable code or instructions stored on and partially executable by the controller C of FIG. 1. At block 252, the controller C causes the infrasensor device 14 to capture at least a predetermined number of optical scans of the subject 12 using a first configuration (i.e., settings) of the infrasensor device 14.

Proceeding to block 254, the measurements from the optical scans are analyzed to identify one or more differentiators, e.g., spikes, dips, trends, or any other statistically relevant markers. The differentiators are identified using machine learning, in one or more examples. In some examples, temporal analysis of time series data using recurrent neural network (RNN) is performed to identify the one or more differentiators. In some examples, the RNN identifies various differentiators that can serve as predetermined thresholds (delta values) for appropriate trigger actions (higher frequency monitoring and analysis/alerts/notifications/reporting.

Proceeding to block 256, the controller C adjusts one or more settings of the infrasensor device 14 to generate a second inframarker configuration. In some embodiments, the second inframarker configuration is generated in response to differentiators not being identified using the first inframarker configuration. In some embodiments, the controller C continues to generate additional inframarker configurations until one or more differentiators are identified. Alternatively, or in addition, the controller C generates at least a predetermined number of inframarker configurations. One or more differentiators are sought (see block 254) after each change in configuration.

Proceeding to block 258, after a predetermined number of configurations, after a predetermined duration, or in response to a manual intervention, the controller C exits the loop (254, 256), and outputs the identified differentiators. In some embodiments, the configuration of the infrasensor device 14 for identifying a physiological state is used automatically when a subject 12 with that physiological state is being monitored by the infrasensor device 14.

The controller C may be adapted to determine, based on the sensor signals, an automated mapping between a phenotype for the patho-physiological condition (e.g., biomarker trends, phases of a disease, etc.) and inframarker absorption intensities to identify an optimal inframarker configuration for detecting this condition. An "inframarker configuration" includes one or more settings of the infrasensor device 14 to capture measurements (e.g., absorption, reflection, etc.) for an inframarker using total internal reflection. In some embodiments, the measurements captured for an inframarker can be a set of one or more units of wavelength in the optical scan/measurements (i.e., infraspectral scan).

The inframarker configuration can further include a value of a "delta" associated with an inframarker, wherein the delta is a dynamic range used to determine if there is a spike/dip in the inframarker measurement, which corresponds to a spike/dip in the amount of the corresponding biomarker in the subject 12. In some embodiments, the controller C performs the identification of the inframarker configuration, including determining the delta, using static algorithms or dynamic algorithms. Here, the inframarker absorption intensities are obtained based on the measurements from the optical sensor 50 of the infrasensor device 14. In some embodiments, an inframarker can be a predetermined set of one or more wavelengths in the optical measurements (i.e., infraspectral scan) of the infrasensor device 14. The identification of the configuration is performed using machine learning (e.g., neural network) in some embodiments, or adjusted by clinicians via a visualization tool by the controller C.

Figure 8:
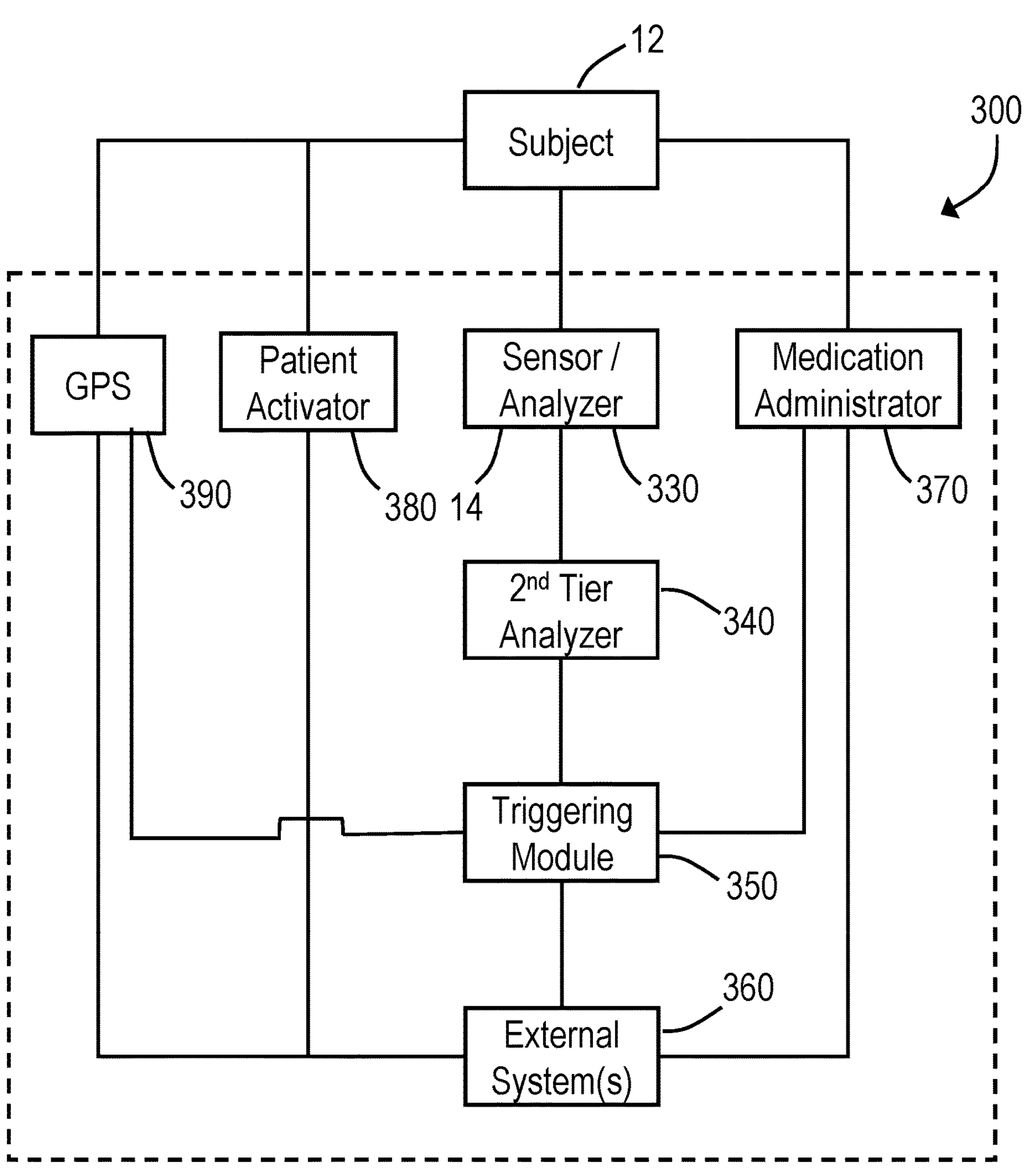
FIGS. 8, 9, and 10 are schematic diagrams respectively illustrating various modular structural arrangements employable by the system of FIG. 1.
Figure 9:
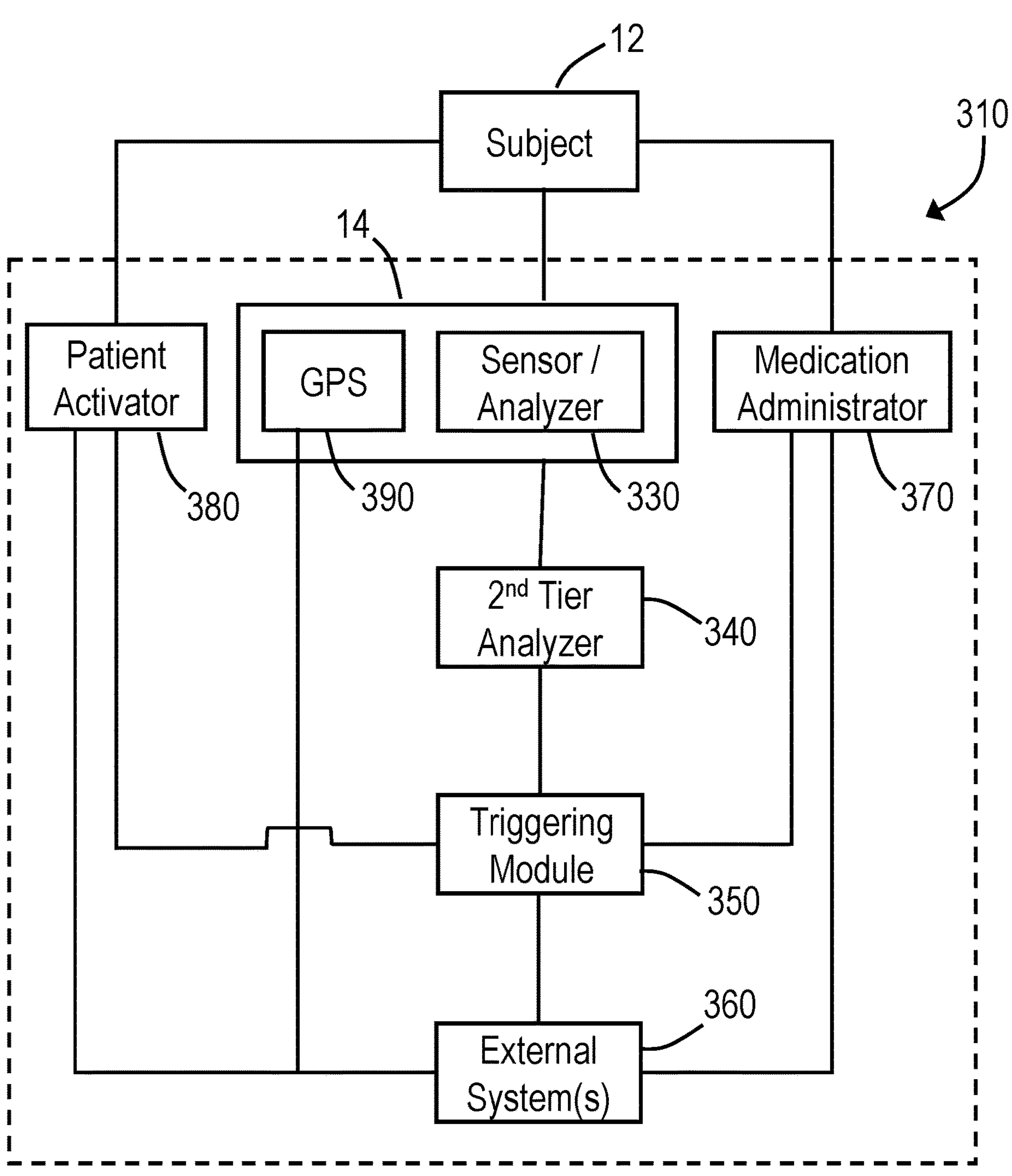
Figure 10:
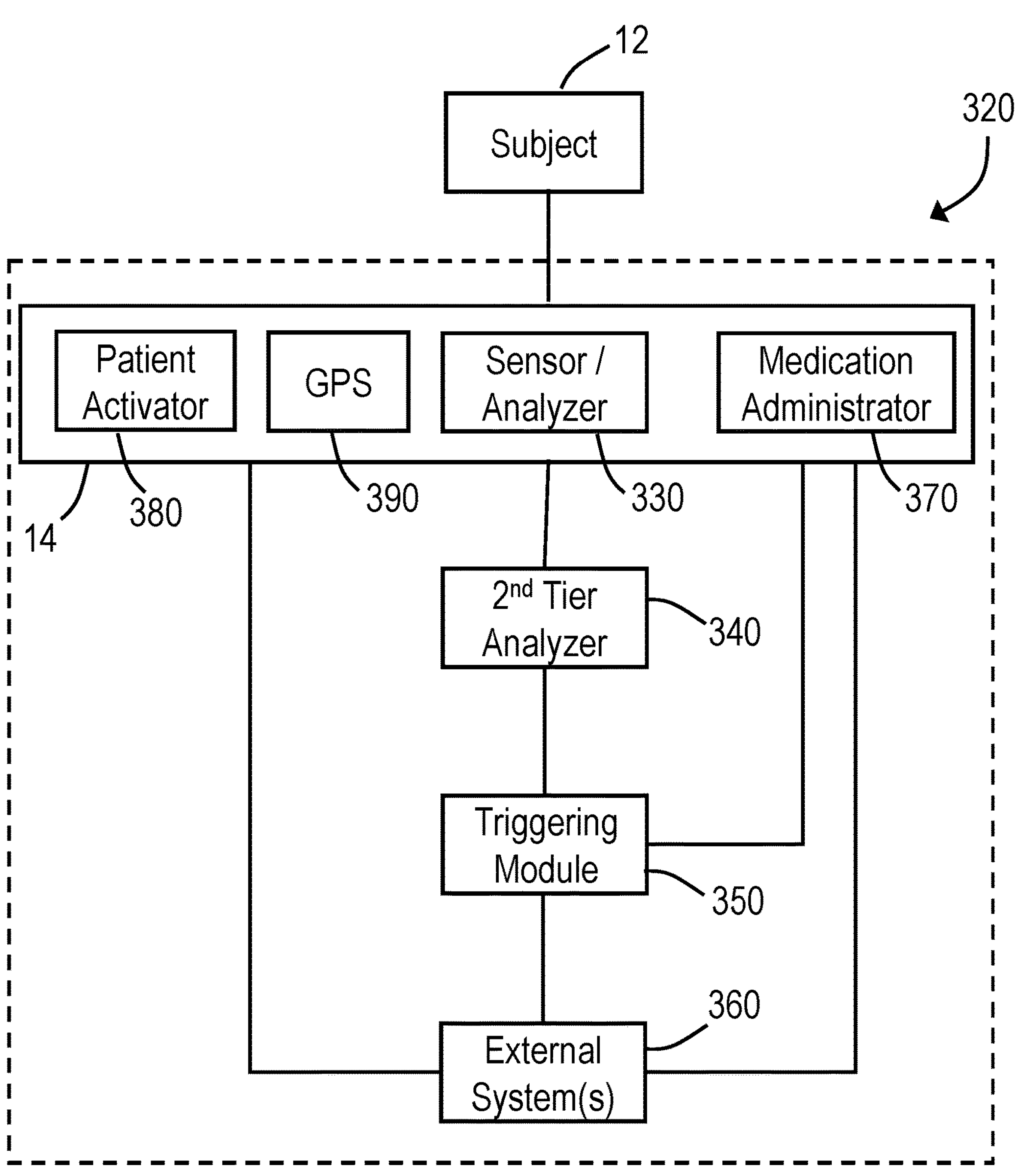

Referring now to FIGS. 8-10, three example modular structures 300, 310, 320 implementable by the system 10 are shown. The modular structures 300, 310, 320 include an infrasensor device 14 having a first-tier sensor 330 adapted to sense a first input related to myocardial function of a subject 12. The first-tier sensor 330 is adapted to produce a first-tier trigger signal when the first input indicates a change in myocardial state from a pathophysiologic baseline, such as a form of cardiac arrhythmia, or myocardial ischemia, or acute myocardial infarction, or acute heart failure, or cardiotoxicity etc. In one example, the first-tier sensor 330 includes an inframarker sensor/analyzer, where the inframarker being sensed and analyzed is indicative of a biomarker of a pathophysiological state of the subject 12.

Referring to FIGS. 8-10, the first-tier trigger signal is output to a second-tier analyzer 340 for analysis. The second-tier analyzer 340 receives the first-tier trigger signal and is configured to reconcile the first-tier trigger signal output from the first-tier sensor 330, and to produce a second-tier signal transmitted to a triggering module 350. The second-tier analyzer 340 can include the controller C and/or the software applications 32. In one example, the second-tier analyzer 340 is in wireless communication with the first-tier sensor 330, for example, via Bluetooth. The triggering element module 350 is adapted to produce a response-invoking signal in response to the second-tier signal. The response-invoking signal may invoke a patient alert, a message to an external system 360, and/or a therapeutic modulation; wherein, the patient alert could posit a patient activator 380 in order to modulate a daily activity or stressor levels, a message to an external system 360 could advance a first responder activator in order to provide immediate clinical attention and response to the subject 12, a therapeutic modulation could advance an actionable notification for the subject 12 to adjust the dosage and administer a medication.

In one example, the subject 12 may manually adjust dosage and/or medication. In another example, the response-invoking signal can be output to a medication administrator 370, such as an injectable or pump to action the medication administrator 370 to deliver therapeutic medication to the subject 12 in the adjusted dosage. In an example, the second-tier analyzer 340 includes software and algorithms to analyze inframarkers in a personalized baseline state of pathophysiology of a subject 12. In another example, the second-tier analyzer 340 includes software and algorithms to analyze inframarkers in various disease phenotypes such as acute or chronic stages of ischemic heart disease or heart failure, and various forms of cardiac arrhythmias. In yet another example, the second-tier analyzer 340 includes software and algorithms to analyze inframarkers as they transition from stable/chronic to unstable/emergent/acute stages.

The second-tier analyzer 340 can be configured to calculate therapeutic dosage appropriate to the detected acuity level of a particular subject 12. The recommended therapeutic agents could be self-administered by a patient/subject 12. The medication administrator 370 may be integrated with an automated injection device 42 (see FIG. 1). In one example, a thrombolytic can be administered by the automated injection device 42 during a silent heart attack in a high risk coronary artery disease patient in the middle of the night or early hours of the morning when cortisol levels could trigger a cascade of atherosclerotic events. The system 10 may automatically inform a remote emergency service provider if the second-tier analyzer 340 determines that the detected inframarkers presents a potential danger to the subject 12 and can inform if and when a therapeutic dosage was modulated.

The modular structures 300, 310, 320 can include a GPS receiver 390 that detects the location of the infrasensor device 14, which is transmitted by the infrasensor device 14 to remote emergency services. In FIG. 8, the modular structure 300 includes the infrasensor device 14 having only the first-tier sensor 330. In the modular structure 310 shown in FIG. 9, the GPS receiver 390 may be included with the infrasensor device 14 in contact with by the subject 12. In the modular structure 320 shown in FIG. 10, the infrasensor device 14 further integrates the first-tier sensor 330 with the GPS receiver 390, the patient activator 380 and a medication administrator 370 for delivery of medication directly to the subject 12 via an injectable or pump, thus providing the convenience of integrating these elements into a wearable device 16, such as a watch (see FIG. 1).

The triggering element module 350 can include dosage indication for a particular medication, or a permutation and combination set of medications. The permutation and combination set of medications could be predefined such as a polypill or configured based upon the algorithmic recommendations of the second-tier analyzer. The dosage indication can include, for example, the addition of a medication, the deletion of a medication, an adjustment in the dosage of a medication, etc. A set of medications could include, but are not limited to, thrombolytics, antiplatelets, anticoagulants, ACE inhibitors, Angiotensin receptor blockers, beta blocks, calcium channel blockers, cholesterol lowering medications, lipid lowering medications, digitalis preparations, diuretics, vasodilators, cardiac myosin inhibitors, anthracyclines, steroids, immune checkpoint inhibitors, cryoprotective agents etc.

Examples of transition between disease phenotypes include, but are not limited to, changes in ischemic heart disease state secondary to dislodged plaques or endothelial injury and dysfunction, perioperative myocardial changes post percutaneous intervention or post non-cardiac surgeries incurring significant blood loss, contractility changes in hypertrophic cardiomyopathy secondary to cardiac myosin inhibitors. Algorithmic recommendations to therapeutic adjustments are based upon inframarkers signaling the acuity of the state of the heart of the subject 12.

In addition to management of cardiac issues, such transdermally derived inframarker enabled auto-pharmaceutical nodulations are particularly critical for chronic diseases, including diabetes, hyperlipidemia, asthma, depression, and others, where repetitive drug administrations are required, and a dynamically personalized delivery schedule could improve drug efficacy and decrease drug toxicity. As an example, detection of transitioning from chronic stable ischemic heart disease to acute coronary syndrome by the infrasensor device 14 and/or the second-tier analyzer 340 could actuate modulation of the levels of thrombolytics relative to anticoagulants, or thrombolytics coupled with antiplatelets, until clinical attention can be provided to the subject 12.

It is to be understood that the system 10 may include fewer components than are illustrated in the FIGS or additional components that are not illustrated in the FIGS. (e.g., additional memory components, embedded controllers, modules, additional network interfaces, etc.). Further, the embodiments described herein with respect to the system 10 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Referring to FIG. 1, in some embodiments, an "inframarker configuration" can be discovered by the controller C for certain markers associated with a biological condition and stored in one of more databases 36. For example, a unique combination of infraspectral scan generated peaks for biomarkers, such as FABP (fatty acid binding protein) or CEA (carcinoembryonic antigen), can be identified. It is understood that other biomarkers are possible in other embodiments.

In some embodiments, the inframarker configuration can be identified for a certain inframarker associated with a physiological state when certain conditions are determined to be satisfied using machine learning techniques. For example, the inframarker configuration is generated when the transdermal infrared spectral scans include a vector A (input measurements) that is mapped to known concentrations of a blood based protein as vector B (output). The inframarker configuration includes a vector in latent space that represents the ideal combination of optical measurements (e.g., infraspectral peaks, absorption values, etc.) that generates vector B from vector A. The inframarker configuration could also be generated via static or other dynamic techniques where various combinations of measurements from the transdermal optical scans are correlated with blood concentration levels using techniques such as regression analysis.

In other embodiments, "inframarkers" indicative of a condition (phenotype) can be identified by the controller C and stored in the databases 36. In some embodiments, the delta value facilitates detecting a condition associated with one or more inframarkers indicative of a condition (phenotype). For example, the condition can be a relatively elevated level of an inframarker. For example, the condition can be an elevated Troponin level that is indicative of myocardial infarction, or elevated BNP that is indicative of acute heart failure. It is understood that the above conditions are exemplary, and that other conditions can also be used to identify corresponding inframarkers. A unique combination of infraspectral scan generated peaks (representing multiple biomarkers—these could be CRP, FABP, CTNI, CK-MB) can be identified for each particular condition or a combination of conditions. The identified inframarker(s) in this manner can be referred to as an "inframarker profile" for that condition or combination of conditions. The inframarker profile can also be referred to herein as an infraprofile. The infraprofiles can be identified using the system 10 for a particular condition or a combination of conditions and stored in the databases 36. For example, the inframarker configuration can represent five infraprofiles for five stages of cancer (precancerous, stages 1, 2, 3, 4), respectively. In another example, the inframarker configuration can represent three infraprofiles for, respectively, three stages of heart attack disease progression (baseline stable chronic ischemic heart disease, transient ischemic attack/ischemia, myocardial infarction).

Further, a time series analysis of an infraspectral scan can identify an underlying phase of a disease (another phenotype) using the controller C. For example, a unique combination of optical measurements (e.g., relative peak, dip, etc.) in the transdermal infraspectral scan can identify coronary artery disease in its stable chronic state vs a reversible state of ischemia (acute myocardial injury) vs an irreversible state of ischemia (myocardial infarction) vs an ischemia in a state of reinfarction. In another example, the inframarker(s) facilitate identifying as the abnormal cells of a tumor spread to tissue and involve various levels of lymph nodes before metastasizing i.e., stage 1 cancer vs stage 2 cancer vs stage 3 cancer vs stage 4 cancer. Such identification, of different stages of a disease, can be achieved by using the embodiments of the technical solutions described herein based on different infra markers released by the subject 12 in the different stages. For example, myocardial ischemia can release h-FABP, CRP, suPAR while infarction releases CTNI in addition to hFABP, CRP and suPAR. Stage 3 cancer (localized) releases certain signals and biomarkers while stage 4 (regional spread) and stage 5 (metastasized) release other signals and biomarkers. Based on the detection of these biomarkers (i.e., patho-physiological conditions) transdermally, using infrasensor device 14, and in a continuous manner, technical solutions described herein facilitate improved triage and treatment of the conditions, along with remote patient monitoring for these conditions.

An inframarker configuration can include one or more settings (of the infrasensor device 14) to be used to predict presence (or absence) of the physiological condition such as a biomarker in the subject 12 using a transdermal scan. Typically, in existing techniques, detecting a biomarker is performed using invasive tests such as drawing blood or other types of fluids or matter from the subject. Further, detecting the biomarker is performed offline, in a clean laboratory environment, and can require a delay until the report comes back. This delay can be potentially delaying the subject 12 from receiving treatment, and in some cases, the "correct" treatment based on the information conveyed by the presence/absence of the biomarker.

The settings in the inframarker configuration to predict the physiological condition can include one or more wavelengths of light to be emitted by the infrasensor device 14. The inframarker configuration can further include one or more thresholds respectively for the one or more wavelengths being used to scan the subject 12. A threshold is used to predict whether the subject 12 may have the physiological condition by comparing a corresponding measurement from the sensor 50 with that threshold. In some examples, the prediction may be based on a combination of measurements.

In some cases, the transdermal scan can be performed in a continuous manner by the infrasensor device 14, for example, a transdermal scan is performed at predetermined intervals. Based on the measurements from the continuous monitoring, trends of the biomarkers can be non-invasively determined by the controller C at predetermined intervals. Accordingly, real time analysis and prediction of the biomarker (i.e., physiological condition) of the subject 12 can be performed in a continuous manner, using the infrasensor device 14 and the controller C. Here "continuous manner" includes performing at least two transdermal optical scans every minute in some embodiments. In other words, within a certain predetermined duration, at least two transdermal optical scans are performed, where the predetermined duration can be one of 45 seconds, 60 seconds, 90 seconds, 120 seconds, 150 seconds, 180 seconds, 300 seconds, or any other such predetermined duration. In yet other words, two successive transdermal optical scans are performed within a predetermined interval of each other such as 45 seconds, 60 seconds, 90 seconds, 120 seconds, 150 seconds, 180 seconds, 300 seconds, or any other such predetermined interval. It is understood that other intervals can be selected.

The controller C can access the configurability of the infrasensor device 14 and adjust one or more settings of the infrasensor device 14 and request additional optical scans using the adjusted settings. For example, the adjustments can include changing the wavelengths of light emitted and/or detected, intensity of light, internal angles of reflection, electric voltage applied, electric current, or any other setting that can cause a particular measurement to be captured in a more accurate manner. Such automatic configurability (i.e., adjustment of configuration) of the monitoring device can improve accuracy of detecting a physiological identifier/marker for the subject 12 in the optical scan (i.e., non-invasive, transdermal manner). In some cases, a subject, such as a nurse, clinician, doctor, or any other personnel, can review and/or update the adjustments being made to the infrasensor device 14. For example, the subject can view the adjustments to the settings of the infrasensor device 14 via a subject-interface, for example, a display of the controller C. The subject can make additional changes to the adjusted settings, which are subsequently sent by the controller C to the infrasensor device 14.

Alternatively, or in addition, frequency of capturing the transdermal optical scans can also be changed in response to the delta being within a predetermined range. For example, frequency of capturing and analyzing the transdermal optical scans is lower (e.g., scan every 15 minutes) when the delta is in a first predetermined ("safe") range, whereas when the delta is in a second predetermined ("critical") range, the frequency of capturing and analyzing the transdermal optical scans is adjusted higher (e.g., scan every five minutes). It is understood that additional predetermined ranges and corresponding monitoring frequencies can be used in other embodiments of the technical solutions herein. In some embodiments, in addition to updating the frequency, alert notifications/reports for subject 12 are sent to medical personnel and/or caregivers.

The infrasensor device 14 is configured to scan for biomarkers (i.e., infraspectral markers) associated with the heart. The heart can go through characteristic patho-physiological phases (phenotypes) as follows: baseline normal to coronary artery disease to transient ischemia to myocardial infarction to heart failure. In each of these phenotypes different biomarkers may be expected. So, baseline normal might have baseline troponins; coronary artery disease might have mildly elevated baselines for troponins; transient ischemia might have a subtle rise and fall of troponins while having an appreciable rise in ischemia markers such as FABP, and inflammatory markers like suPar, CRP; myocardial infarction might have an acute rise of troponins, FABP, CRP, suPar. However, the levels of these over time will vary by virtue of their half-life and renal clearance. Heart failure might then have mildly elevated baseline for troponin and another biomarker BNP that is released when the myocardium experiences stretch due to heart's response to increased afterload or preload. Since the levels of these different markers vary in different phases of the diseases, and is further variable based on patient's clinical context that varies with time, the software application 32 (e.g., AI models 34) are configured for deep learning in which the AI models 34 include neural networks (e.g., convolutional neural networks (CNNs)) coupled with time series analysis (long short-term memory (LSTM), recurrent neural network (RNN), etc.) to understand the complex relationships (e.g., a researcher may be unable to see continuous biomarkers that are representative of true underlying patho-physiology). Once the biomarkers for the different phases are determined using the infrasensor devices 14 and controller C, the controller C can cause treatment/medicine to be administered for any subject determined to be experiencing any of the determined patho-physiological phases of the heart.

Using infraspectral markers, one or more inframarker profiles ("infraprofiles") and/or one or more inframarker configurations, the software applications 32 may include and/or be coupled to one or more algorithms configured to perform and provide precision medicine, biomarker discovery, drug discovery, and/or in silico clinical trials as technical solutions.

The embodiments described herein further facilitate personalized triage and alert workflow baseline and trending information. For example, a baseline of the measurements from the infrasensor device 14 for a particular subject 12 can be established by capturing the transdermal optical scans of the subject 12 for at least a predetermined times/duration. For example, once at least 15 transdermal optical scans are performed for the subject 12, those 15 scans are used to establish baseline measurements for a particular biomarker (e.g., troponin I, FABP3, etc.) for the subject 12. Subsequently, further transdermal optical scans (e.g., the 16th scan) of the subject 12 are compared to the established baseline to determine whether a change (delta) in one or more measurements exceeds (spike/dip) a predetermined threshold. In such cases, further actions can be taken for the subject 12. In other examples, instead of a personalized baseline, a predetermined baseline can be used to compare the trends of the measurements of the subject 12. A separate baseline (personalized or predetermined) is used for each measurement captured in the non-invasive transdermal optical scan. In some cases, a personalized baseline (for a particular subject) is used for a first inframarker (e.g., h-FABP) and a predetermined baseline (non-personalized/common across multiple subjects) is used for a second inframarker (e.g., troponin I).

Once one or more transdermal scans of the subject are performed, the controller C can generate an infraprofile of the subject 12 and save it to the database 36 in the cloud unit 24, and associated, for example, in the database 36 with other subject-related information of the subject 12. The subject related information of a subject 12 (such as Patient 1) can include personally identifying information, demographics, risk factors, comorbidities, medications prescribed to or taken by the subject 12, clinical evaluation findings, and/or other data such as vitals obtained from a wearable device, all or some of which can be associated with the infraprofile of the subject 12 and the transdermal scans performed of the subject 12 and/or inframarkers detected for the subject 12. As determined by the controller C, the infraprofile can predict the presence/absence of one or more biomarkers, and in turn, physiological conditions of the subject 12. Based on the infraprofile, a medical personnel (e.g., doctor, nurse, etc.) or the controller C can recommend a treatment, test, etc., for the subject. For example, based on the prediction from the transdermal scan, the medical personnel or the controller C may determine whether an invasive test is required. Alternatively, or in addition, based on the prediction, the medical personnel or the controller C can determine a certain course of treatment for the subject 12.

In some embodiments, the controller C may already know that the subject 12 has a certain physiological state, e.g., a disease. The controller C, in conjunction with the infrasensor device 14, can be used to determine an inframarker configuration (i.e., settings of the infrasensor device 14) that can detect an inframarker in the optical scans for the subject, i.e., a measurement in the subject 12 that corresponds to the physiological state.

Referring now to FIG. 1, the controller C of the system 10 may utilize decentralized data collection from infrasensors (e.g., infrasensor device 14) with inputs for clinical context. Infrasensor generated data (e.g., infraspectral markers) with patient related features is used to build a large dataset (e.g., stored in the databases 36) for different clinical queries (infraprofiles and inframarker configurations). Using the large dataset (e.g., stored in one or more databases 36) for different clinical queries (infraprofiles and inframarker configurations), the controller C and/or software applications can be configured to enable subjects to query different clinical questions to understand the effect of drugs or any other clinical variables.

The controller C may be configured to evaluate a drug or medical device (e.g., delivering a drug or controlling a bodily function such as the heart) by using the infraspectral markers, inframarker profile based on the infraspectral markers, and the inframarker configuration for the infrasensor device 14. The evaluation can determine trending biomarkers, dosage levels, and the functional state of heart remodeling reversal. Additionally, the controller C may identify molecular markers in chronic progressive diseases (such as cardiac and neurological diseases, diabetes, cancer, etc.), acute conditions of interest (such as infectious diseases, heart failures, sepsis, autoimmune diseases, etc.), etc. Targeted treatment can then be provided to the person according to the determined disease or condition. The system 10 enables risk stratification for health care providers, effective risk modeling for payers, better patient outcomes (i.e., successful treatment of diseases), and a lower cost burden to the health system.

In one or more examples, the controller C of the system 10 may utilize centralized data normalization and foundational machine learning architecture. Referring to FIG. 1, various machine learning modules 20, such as those incorporating artificial intelligence (AI) models 34 accessible from the cloud unit 24, may be used with the deep infraomics platform. Additionally, the software application 32 can be configured to perform feature extraction by capturing (after scanning by the infrasensor device 14) the desired infraspectral markers that correlate to the inframarker configuration of interest. Infrasensor (e.g., infrasensor devices 14) along with other wearables (e.g., ECG, vital signs) generate time series data. Foundational deep learning models based on this time series information when coupled with patient features provide a unique view into the patient's patho-physiology of disease progression over time. The software applications 32 (e.g., AI models 34) can be leveraged by different stakeholders such as pharma companies to query the data to ask different questions, to simulate different scenarios, and/or to perform in silico clinical trials.

In some embodiments, the controller C may operate as a transdermal biomarker detection platform that uses deep infraomics. The controller C has access to one or more software applications 32 (shown in FIG. 1) configured to perform deep infraomics, along with any of the analysis discussed herein. Deep infraomics, as that term is used herein, is artificial intelligence based a digital platform that builds on top of infraomics. Infraomics, as that term is used herein, is the study of infraspectral markers ("inframarkers", e.g., molecular markers characterized by infrared wavelengths), inframarker profiles ("infraprofiles", e.g., for a specific disease phenotype), and inframarker configurations (e.g., the characterization of disease progression including phases of cardiovascular disease, neurological disease, cancer, etc.).

Further regarding use of the controller C and infrasensor devices 14 for facilitating in silico trials, the software application 32 using deep infraomics provides advanced mathematical modeling on a proprietary dataset (e.g., stored in databases 36) that includes time series infraspectral markers, infraprofiles, and inframarker configurations through the patient life cycle of disease, along with the clinical context around disease management, clinical findings, drug dosage, demographics, and risk factors. The software applications 32 can perform retrospective and prospective analysis, which allow drug companies and research institutions to run in-silico trials to accelerate the evaluation of new drugs and/or medical devices and/or interventions prior to in-human trials. Using the software applications 32, deep infraomics generates prognosis scores and extrapolates clinical end points for drug and device manufacturers, regulatory bodies, and payers to assess investment into new drugs and pharmaceuticals. By visualizing patient impact, deep infraomics will enable researchers and healthcare providers in determining appropriate dosage of a pharmacologic therapeutic or the optimal time to intervene with a procedure (treatment plan), thereby personalizing care workflows based on patient baselines. The treatment plan can be further modulated on a frequent basis, based on the patient's dynamic infraprofile.

In one or more embodiments, one or more algorithms of the controller C and/or software applications 32 individually and/or working in any combination may be implemented as so-called classifiers. Examples of suitable classifiers include but are not limited to neural networks (described in greater detail below), support vector machines (SVMs), logistic regression, decision trees, hidden Markov Models (HMMs), etc. The end result of the classifier's operations, i.e., the "classification," is to predict a class for the data. The ML algorithms apply machine learning techniques to the received data in order to, over time, create, train, and update a unique "model." The learning or training performed by the software applications 32 can be supervised, unsupervised, or a hybrid that includes embodiments of supervised and unsupervised learning. Supervised learning is when training data is already available and classified/labeled. Unsupervised learning is when training data is not classified/labeled so must be developed through iterations of the classifier. Unsupervised learning can utilize additional learning/training methods including, for example, clustering, anomaly detection, neural networks, deep learning, and the like.

The personalized assistance system 10 may be configured to be "adaptive" and may be updated periodically after the collection of additional data. In other words, the machine learning models 20 may be configured to be "adaptive machine learning" algorithms that are not static and that improve after additional subject data is collected. The machine learning modules 20 may include a mix of different types of machine learning models. The machine learning modules 20 of FIG. 1 may include at least one neural network, an example of which is shown in FIG. 11.

Figure 11:
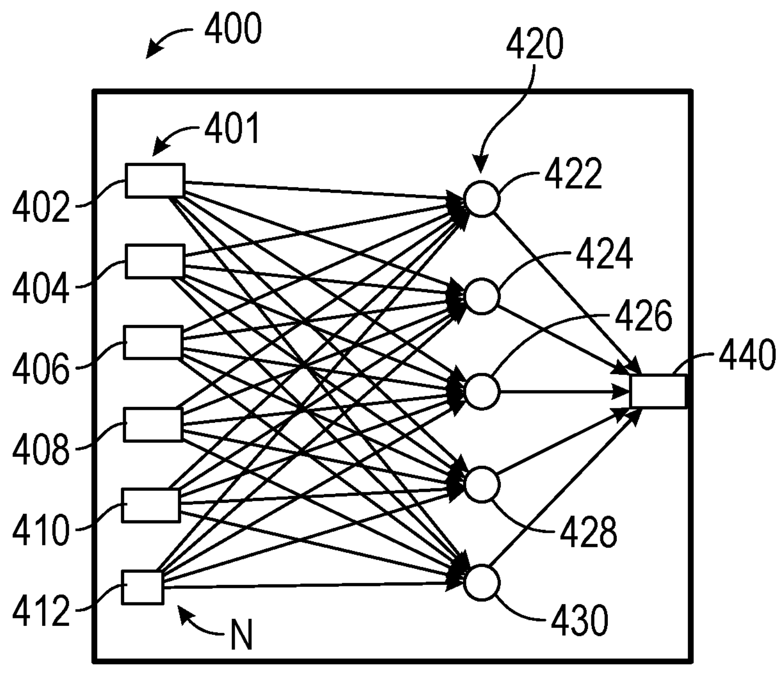
FIG. 11 is a schematic diagram of an example machine learning model executable by the controller of FIG. 1.

Referring to FIG. 11, the neural network 400 is a feed-forward artificial neural network having at least three layers, including an input layer 401, at least one hidden layer 420 and an output layer 440. Each layer is composed of respective nodes N configured to perform an affine transformation of a linear sum of inputs. The respective nodes N are characterized by a respective bias and respective weighted links. The parameters of each respective node N may be independent of others, i.e., characterized by a unique set of weights. The input layer 401 may include first input node 402, second input node 404, third input node 406, fourth input node 408, fifth input node 410 and sixth input node 412. The respective nodes N in the input layer 401 receive the input, normalize them and forward them to respective nodes N in the hidden layer 420.

Referring to FIG. 11, the hidden layer 420 may include a first hidden node 422, second hidden node 424, third hidden node 426, fourth hidden node 428 and fifth hidden node 430. Each respective node N in a subsequent layer computes a linear combination of the outputs of the previous layer. A network with three layers would form an activation function $f(x)=f(3)(f(2)(f(1)(x)))$. The activation function $f$ may be linear for the respective nodes N in the output layer 440. The activation function $f$ may be a sigmoid for the hidden layer 420. A linear combination of sigmoids may be used to approximate a continuous function characterizing the output vector y. The patterns recognized by the neural network 400 may be translated or converted into numerical form and embedded in vectors or matrices.

Figure 12:
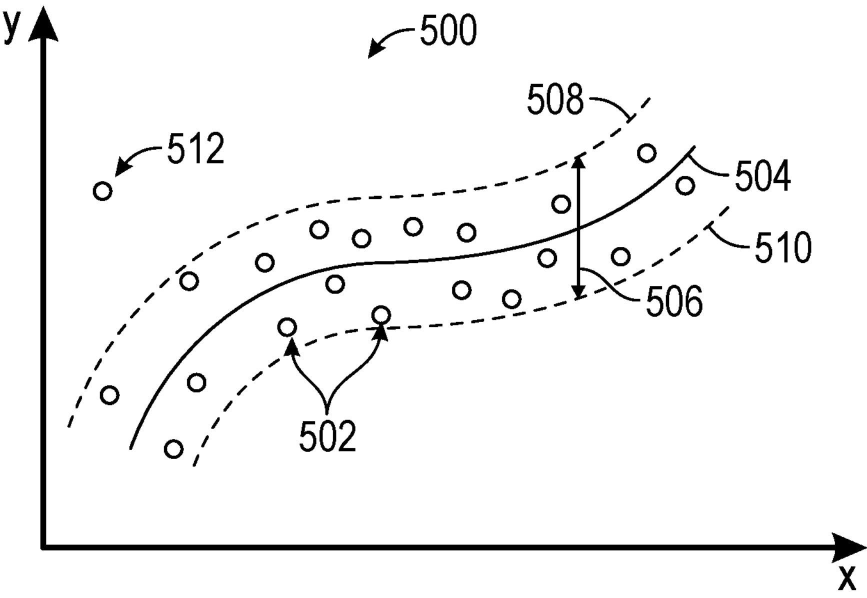
FIG. 12 is a schematic diagram of another example machine learning model executable by the controller of FIG. 1.

The machine learning modules 20 may incorporate a support vector regression model 500, an example of which is shown in FIG. 12. The support vector regression model 500 is configured to find a function (hyperplane 504 in FIG. 12) such that the data points 502 are within a margin 506 from this function, i.e., inside a first boundary line 508 and a second boundary line 510. Referring to FIG. 12, the hyperplane 504 may be defined as the line that will match the input vector x to the output vector y, i.e., predict a target value. The hyperplane 504 is individualized so as to maximize the margin 506 and minimize a predefined error. If there are points (such as extraneous point 512) that are outside the margin 506, a penalty may be built into the support vector regression model 500. Prior to ascertaining the hyperplane 504, the support vector regression model 500 may employ a kernel function to map a lower dimensional dataset into a higher dimensional dataset. Other machine learning models available to those skilled in the art may be employed.

In some embodiments where the machine learning modules 20 are implemented as neural networks, a resistive switching device (RSD) can be used as a connection (synapse) between a pre-neuron and a post-neuron, thus representing the connection weight in the form of device resistance. The machine learning modules 20 may employ at least one deep learning map to match an input vector x to an output vector y by learning an activation function $f$ such that $f(x)$ maps to y. A training process enables the machine learning modules 20 to correlate the appropriate activation function $f(x)$ for transforming the input vector x to the output vector y. For example, in the case of a simple linear regression model, two parameters are learned: a bias and a slope. The bias is the level of the output vector y when the input vector x is 0 and the slope is the rate of predicted increase or decrease in the output vector y for each unit increase in the input vector x. Once the machine learning modules 20 are respectively trained, estimated values of the output vector y may be computed with new values of the input vector x.

Referring to FIG. 1, the network 40 may be wireless or may include physical components and may be a short-range network or a long-range network. For example, the network 40 may be implemented in the form of a local area network which may include, but is not limited to, a Controller Area Network (CAN), a Controller Area Network with Flexible Data Rate (CAN-FD), Ethernet, blue tooth, WIFI and other forms of data connection. The local area network may be a Bluetooth™ connection, defined as being a short-range radio technology (or wireless technology) aimed at simplifying communications among Internet devices and between devices and the Internet. Bluetooth™ is an open wireless technology standard for transmitting fixed and mobile electronic device data over short distances and creates personal networks operating within the 2.4 GHz band. The local area network may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

Various embodiments of the technical solutions are described herein with reference to the related drawings. Alternative embodiments of the technical solutions can be devised without departing from the scope of the technical solutions presented herein. Various connections and positional relationships (e.g., over, below, adjacent, etc.) are set forth between elements in the following description and in the drawings. These connections and/or positional relationships, unless specified otherwise, can be direct or indirect, and the present technical solutions are not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, a physical medium with patterns of holes, a RAM, a PROM, an EPROM, a FLASH-EEPROM, other memory chip or cartridge, or other medium from which a computer can read.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technical solutions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the subject's computer, partly on the subject's computer, as a stand-alone software package, partly on the subject's computer and partly on a remote computer or entirely on the remote computer or server. In the latter scenario, the remote computer may be connected to the subject's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform embodiments of the present technical solutions.

The flowcharts shown in the FIG(S). illustrate an architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by specific purpose hardware-based systems that perform the specified functions or acts, or combinations of specific purpose hardware and computer instructions. These computer program instructions may also be stored in a computer-readable medium that can direct a controller or other programmable data processing apparatus to function in a particular manner, such that the instructions stored in the computer-readable medium produce an article of manufacture including instructions to implement the function/act specified in the flowchart and/or block diagram blocks.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings, or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A personalized assistance system for monitoring and providing controlled responses to a physiological state of a subject, the system comprising:

an infrasensor device adapted to collect input data from a subject, the infrasensor device having an infrared source configured to emit infrared light and an internal reflection element (IRE) optically coupled to the infrared source, the IRE being formed of a material having a refractive index that defines a critical angle for the infrared light;

a controller configured to receive the input data, the controller being adapted to selectively execute one or more machine learning modules;

wherein the infrasensor device is configured such that the infrared light is incident on an interface of the IRE at an angle equal to or less than the critical angle to produce total internal reflection, and such that the totally internally reflected infrared light penetrates an epidermis of the subject to a depth determined by the refractive index of the IRE, the refractive index of the epidermis, and a wavelength of the infrared light;

wherein the controller has a processor and tangible, non-transitory memory on which instructions are recorded, the controller being adapted to:

extract one or more inframarkers from the input data from the infrasensor device, wherein the inframarkers are optical infrared signatures indicating a single one or a combination of biomarkers representing the physiological state of the subject, the physiological state including myocardial injury and/or myocardial stress;

determine respective changes in the one or more inframarkers in real-time, including deviations from a respective baseline measurement customized for the subject;

determine at least one recommendation based in part on the one or more inframarkers and the respective changes, via the one or more machine learning modules; and execute the at least one recommendation when a predefined threshold is met.

2. The system of claim 1, wherein:

the infrared source is configured to generate light at a predetermined pulse rate, the infrasensor device being adapted to employ infrared spectroscopy at a wavelength range between 5 micrometers and 12.5 micrometers; and the infrasensor device includes a photodetector configured to detect the light at a predetermined polling rate.

3. The system of claim 1, further comprising:

a dialysis apparatus selectively connected to the subject, the infrasensor device being positioned concurrently with dialysis, the infrasensor device being positioned transdermally or integrated upstream or downstream of the dialysis apparatus or within respective components of the dialysis apparatus;

wherein the controller is employed in post-dialysis drug re-equilibration, including monitoring changes in drug concentration in the subject post-dialysis.

4. The system of claim 1, further comprising:

an extracorporeal membrane oxygenation (ECMO) apparatus selectively connected to the subject, the ECMO apparatus including a pump and an oxygenator;

wherein the infrasensor device is positioned concurrently with dialysis, the infrasensor device being positioned transdermally or integrated upstream or downstream of the ECMO apparatus or within respective components of the ECMO apparatus; and wherein the controller is adapted to generate automatic threshold-based trigger notifications to the ECMO apparatus for optimal drug dosing for the subject based in part on the respective changes in the one or more inframarkers.

5. The system of claim 1, further comprising:

a patient activator in communication with the controller, the patient activator including a display and/or audio output for communication with the subject; and wherein executing the at least one recommendation includes providing messages and/or alerts to the subject, including dosage modulation instructions, via the patient activator.

6. The system of claim 1, further comprising:

an injection device in communication with the controller and adapted to deliver a therapeutic medication to the subject; and wherein executing the at least one recommendation includes automatic adjustment of the therapeutic medication to the subject, via the injection device.

7. The system of claim 6, wherein the injection device is an analgesia pump for pain management.

8. The system of claim 6, wherein:

the controller is adapted to calculate a therapeutic dosage appropriate to a detected acuity level of the one or more inframarkers; and the therapeutic medication includes at least one of thrombolytics, anticoagulants, antiplatelets, thrombolytics coupled with antiplatelets, the therapeutic medication being automatically administered when the detected acuity level exceeds a threshold.

9. The system of claim 6, wherein the one or more inframarkers include troponin, the therapeutic medication including at least one of beta blockers, calcium channel blockers, loop diuretics, and spironolactones.

10. The system of claim 1, wherein:

the subject is receiving immune checkpoint inhibitor therapy; and wherein executing the at least one recommendation includes automatic down-titration of the immune checkpoint inhibitor therapy, and initiating a modulated steroid therapy, when the one or more inframarkers exceed a predefined ceiling.

11. The system of claim 1, wherein:

the one or more inframarkers include at least one of extracellular vesicles, co-receptors for growth factors, cell surface receptor adaptor proteins, transcription factors, and scaffolding proteins; and the controller is adapted to monitor cancer progression and/or therapy resistance for the subject based in part on the one or more inframarkers.

12. The system of claim 1, wherein the one or more inframarkers include troponin, the controller being adapted to assess cardiotoxicity in the subject based in part on the one or more inframarkers.

13. The system of claim 1, further comprising:

a GPS receiver adapted to detect location of the infrasensor device; and wherein executing the at least one recommendation includes automatic notification of a remote assistance service provider.

14. A method for operating a personalized assistance system of monitoring and providing controlled responses to a physiological state of a subject, the system having a controller with a processor and tangible, non-transitory memory on which instructions are recorded, the method comprising:

collecting input data from a subject via an infrasensor device electronically coupled with the controller, the infrasensor device having an infrared source configured to emit infrared light and an internal reflection element (IRE) optically coupled to the infrared source, the IRE being formed of a material having a refractive index that defines a critical angle for the infrared light;

operating the infrasensor device such that the infrared light is incident on an interface of the IRE at an angle equal to or less than the critical angle to produce total internal reflection, and such that the totally internally reflected infrared light penetrates an epidermis of the subject to a depth determined by the refractive index of the IRE, the refractive index of the epidermis, and a wavelength of the infrared light;

transmitting the input data to the controller;

extracting one or more inframarkers from the input data from the infrasensor device, via execution of a software application by the controller, wherein the inframarkers are optical infrared signatures indicating a single one or a combination of biomarkers representing the physiological state of the subject, the physiological state including myocardial injury and/or myocardial stress;

determining respective changes in the one or more inframarkers in real-time, via the controller, including deviations from a respective baseline measurement customized for the subject;

determining at least one recommendation based in part on the one or more inframarkers and the respective changes, via execution of one or more machine learning modules by the controller; and executing the at least one recommendation when a predefined threshold is met.

15. The method of claim 14, further comprising:

incorporating a transdermal sensor in the infrasensor device, the transdermal sensor being configured to be in transdermal contact with the subject; and operating the infrasensor device at a wavelength range between 5 micrometers and 12.5 micrometers.

16. The method of claim 14, further comprising:

selectively connecting an extracorporeal membrane oxygenation (ECMO) apparatus to the subject, the ECMO apparatus including a pump and an oxygenator;

positioning the infrasensor device upstream or downstream of the ECMO apparatus or within respective components of the ECMO apparatus; and generating automatic threshold-based trigger notifications to the ECMO apparatus based in part on the respective changes in the one or more inframarkers.

17. The method of claim 14, further comprising:

calculating a dosage level for a therapeutic medication appropriate to a detected acuity level of the one or more inframarkers, via the controller; and automatically administering the therapeutic medication, via an injection device, when the detected acuity level exceeds a threshold, the therapeutic medication including at least one of thrombolytics, anticoagulants, and thrombolytics coupled with antiplatelets.

18. The system of claim 1, wherein the infrasensor device is adapted to employ infrared spectroscopy at a wavelength range between 5 micrometers and 12.5 micrometers.

19. The system of claim 18, wherein:

the infrasensor device is adapted to perform one or more transdermal scans of the subject; and the controller is adapted to analyze optical measurement features from the transdermal scans, including relative spectral peaks and/or relative spectral dips, and to identify a cardiovascular condition selected from stable chronic coronary artery disease, reversible ischemia, irreversible ischemia, and reinfarction based on the optical measurement features.

20. The method of claim 14, further comprising:

performing one or more transdermal scans of the subject, via the infrasensor device;

analyzing optical measurement features from the transdermal scans, including relative spectral peaks and/or relative spectral dips, via the controller; and identifying a cardiovascular condition selected from stable chronic coronary artery disease, reversible ischemia, irreversible ischemia, and reinfarction, based on the optical measurement features, via the controller.

* * * * *